United States Patent
Ryazanov et al.

(10) Patent No.: US 6,346,406 B1
(45) Date of Patent: Feb. 12, 2002

(54) ELONGATION FACTOR-2 KINASE (EF-2 KINASE), AND METHODS OF USE THEREFOR

(75) Inventors: Alexey G. Ryazanov; William N. Hait, both of Princeton; Karen S. Pavur, Highland Park, all of NJ (US)

(73) Assignee: University of Medicine & Dentistry of New Jersey, Newark, NJ (US)

( * ) Notice: Subject to any disclaimer, the term of this patent is extended or adjusted under 35 U.S.C. 154(b) by 0 days.

(21) Appl. No.: 08/914,999

(22) Filed: Aug. 20, 1997

(51) Int. Cl.[7] .................... C12N 9/12; C12N 15/54; C12Q 1/48; G01N 33/53

(52) U.S. Cl. .................... 435/194; 435/6; 435/7.1; 435/15; 536/23.2

(58) Field of Search ................ 435/6, 7.1, 194, 435/15

(56) References Cited

PUBLICATIONS

Perryman, M.B., et al., 1986, Biochemical and Biophysical Research Communications, vol. 140, "Isolation and sequence analysis of a full–length cDNA for human M creatine kinase", pp. 981–989.*

Cheng, N., et al., 1987, Journal of Cellular Biochemistry, vol. 35, "Uridine kinase: Altered subunit size or enzyme expression as a function of cell type, growth stimulation, or mutagenesis", pp. 217–229.*

Takazawa, K., et al., 1991, Biochemical Journal, vol. 278, "Molecular cloning and expression of a new putative inositol 1,4,5–triphosphate 3–kinase isoenzyme", pp. 883–886.*

Bowers, B.J., et al., 1993, Gene, vol. 123, "Isolation and sequence of a mouse brain cDNA coding for protein kinase C–(gamma) isozyme", pp. 263–265.*

Ropp, P.A., et al., 1996, Archives of Biochemistry and Biophysics, vol. 336, "Cloning and expression of a cDNA encoding a uridine kinase from mouse brain", pp. 105–112.*

Bagaglio, D. M., et al., Cancer Reserch, vol. 53, "Phosphorylation of elongation factor 2 in normal and malignant rat glial cells", pp. 2260–2264, 1993.*

Albarracin, C. T., et al., The Journal of Biological Chemistry, vol. 269, "Prolactin regulation of the calmodulin–dependent protein kinase III elongation factor–2 system in the rat corpus luteum", pp. 7772–7776, 1994.*

(List continued on next page.)

Primary Examiner—Ponnathapu Achutamurthy
Assistant Examiner—William W. Moore
(74) Attorney, Agent, or Firm—Christine E. Dietzel; Klauber & Jackson

(57) ABSTRACT

A new superfamily of protein kinases has been discovered that centers around eukaryotic elongation factor-2 kinase (eEF-2 kinase). The protein kinases of this new superfamily have the following characteristics: 1) sequence similarity to eEF-2 kinase; 2) no sequence similarity to the protein kinases of either the serine/threonine/tyrosine kinase or histidine kinase superfamily; and, 3) specifically phosphorylates α-helical regions of proteins as opposed to β-turns, as seen in all other protein kinases. Assays have been developed utilizing eEF-2 kinase and a phosphorylation target consisting of a novel α-helical 16-amino acid peptide sequence to facilitate high-throughput screening for compounds that can specifically inhibit this protein kinase that has been implicated tumor growth and other hyperproliferitive disorders. Additionally, the disclosed invention includes assessing eEF-2 kinase levels for diagnostic purposes, and therapeutic formulations to inhibit eEF-2 kinase activity.

17 Claims, 10 Drawing Sheets

OTHER PUBLICATIONS

Redpath, N. T., et al., The EMBO Journal, vol. 15, "Regulation of translation elongation factor–2 by insulin via a rapamycin–sensitive signalling pathway", pp. 2291–2297, 1996.*

Parmer, T. G., et al., Proceedings of the American Association for Cancer Research, vol. 37, "Calmodulin–dependent protein kinase III–mediated phosphorylation of elongation factor 3 in human breast cancer", p. 12, Abstract No. 81, 1996.*

Redpath, N. T., et al., The Journal of Biological Chemistry, vol. 271, "Cloning and expression of cDNA encoding protein synthesis elongation factor–2 kinase", pp. 17547–17554, 1996.*

Hait, W. N., et al., FEBS Letters, vol. 397, "Elongation factor–2 kinase: immunological evidence for the existence of tissue–specific isoforms", pp. 55–60, 1996.*

Clancy, C. E., et al., The Journal of Biological Chemistry, vol. 272, "Identification of a protein kinase from Dictyostelium with homology to the novel catalytic domain of myosin heavy chain kinase A", pp. 11812–11815, 1997.*

Ryazanov, A. G., et al., Proceedings of the National Academy of Sciences, U.S.A., vol. 94, "Identification of a new class of protein kinases represented by eukaryotic elongation factor–2 kinase", pp. 4884–4889, 1997.*

* cited by examiner

FIG. 1A

```
                              I
human EF2K  122  GEWLDDEVLIKMASQPFGRGAMRECFRTKKLSNFLHAQ----------------------QWKGASNYVAKRYIEPVD
C. e. EF2K  108  KQWTEDIVDVRLHPDSFARGAMRECYRLKKCSKHGTSQ----------------------DW--SSNYVAKRYICQVD
MHCK A      570  NKWIRLSMKLKVERKPFAEGALREAYHTVSLGVGTDENYPLGTTKLFPPIEMISPISKNNEAMTQLKNGTKFVLKLYKKEAE
MHCK B      130  AQWTCTATLVKVEPVPFAEGAFRKAYHTLDLSKSGA-----------------------------SGRYVSKIGKK--
FC-AN09       1      IVCVSIEKTPFAKGSCRTAHKLKDWSQP--------------------------------DQGLVGKFSTNKK-
consensus        W**o*o**FGRo***************************************oV*K*******

II
                                      III                                        IV
human EF2K  178  ----RDVYFEDVRLQMEAKLWGEEYNRHKPPKQVDIMQMCIIELKDR-----PGKPLF-HLEHYIEGKYIKYNSNSGFVRDDNI
C. e. EF2K  162  ----RRVLFEDDVRLQMDAKLWAEEYNRYNPPKKIDIVQMCVIEMIDV----KGSPLY-HLEHFIEGKYIKYNSNSGFVSNAA-
MHCK A      653  QQASRELYFEDVKMQMVCRDWGNKFNQKPPKKIEFLMSWVVELIDRSPSSNGQPILCSIEPLLVGEFKKNNSNYGAVLTN--
MHCK B      177  -PTPRPSYFEDVKMQMIAKKWADKYNSFKPPKKIEFLQSCVLEFVDRTSSD----LICGAEPYVEGQYRKYNNNSGFVSNDE-
FC-AN09      42  --TTRDSYFTDVLMQTFCAKWAEKFNEAKPPKPITFLPSYVYELIDHPPPY---PV-CGGEPFIEGDYKKHNNNSGYVSSDA-
consensus        ****R**oF*DV*oQ*****W****N***PPK*o*oo***ooEo*D******oo*G*o**E*oo*G*o*K*N*N*G*V****

V                                        VI
human EF2K  252  RLTPQAFSHFTFERSGHQLIVVDIQGVGDLYTDPQIHTETGTDFEGDGNLGVRGMALFFYSHACNRICESMGLAPFDLSPRERD
C. e. EF2K  235  RLTPQAFSHFTFERSGHQMMVVDIQGVGDLYTDPQIHTVVGTDYGDGNLGTRGMALFFHSHRCNDICETMDLSNFELSPPEIE
MHCK A      734  RSTPQAFSHFTYELSNKQMIVVDIQGVDDLYTDPQIHTPDGKGFGLGNLGKAGINKFITTHKCNAVCALLDL-DVKLG----
MHCK B      254  RNTPQSFSHFTYEHSNHQLLIDIQGVGDHYTDPQIHTYDGVGFGIGNLGQKGFEKFLDTHKCNAICQYINLQSIN------
FC-AN09     118  RNTPQSFSHFSYELSNHELLIVDIQGVNDFYTDPQIHTKSGEGFGEGNLGETGFHKFLQTHKCNPVCDFLKLKPIN------
consensus        R*TPQ*FSHF*oE*S***ooooDIQGV*DoYTDPQIHTGoG*GNLGGoG*Fo**H*CN*oC**o*Lo***

VII
human EF2K  335  AVNQNTKLLQSAKT---ILRGTEEKCGS
C. e. EF2K  318  ATEVAMEVAAKQKKSCIVPPTVFEARR
MHCK A      811  -----GVLSGNNKKQ--LQQGTMVMPDI
MHCK B      330  ---------PKSEKSDC---GTVPRPDL
FC-AN09     194  ---------QSKKA--LLRGTLPVVQL
consensus        ****************T*******
```

FIG. 5A

```
                                                                                              R.......QSP.....DG...G....E..........
human eEF-2K     1   ................................................MTID TTNESDNSPTNSPGLEA SARTFSLNASKMVR----ITD    44
C. elegans eEF-2K 1  ......................................................MADE DLIFCLEGVDGGRCSRA GHNADSDTDS DDEGYFICPITD     38
mouse eEF-2K     1   ................................................MADE DLIFCLEGVDGGRCSRA GHNADSDTDS DDEGYFICPITD     44

PS........N....NK..........S.RY.SS........N.....Q.......
human eEF-2K     45  DYADEVFI EQNDVVIEKPRMD----------- PLHVRKLMETWR KAARRART       93
C. elegans eEF-2K 39 ........................................................Q.   79
mouse eEF-2K     45  DHMSNQNV SSKVQSYYSNLTKTECGS-TGSP ASSFHFKEAW KHAIEKAK-       92

R.........D.....
human eEF-2K     94  NYIDPWDEEN IHEYPVQRAKRYR YSA IRKQWTED IVDVRLIHPDS FARGAM    143
C. elegans eEF-2K 80 HMPDPWAEEH ILEDIATEHA TRHRYNAVT GEWLIKDEVLIK ASQPFGRAM    129
mouse eEF-2K     93  ..............WIRLSM KLK VERKPFAE GAL                      142
MHCK A         572  _____      591

R........E.
human eEF-2K    144  RECYRLKKCS................KHGTSQDW--SSN                   166
C. elegans eEF-2K 130 RECERTKKLS................NELHAQQWKGASN                  150
mouse eEF-2K    143  REAYHTVSL GVGTDENYPLGTTTKLFPPIEMISPISKN NEAMTQLKNGUK       165
MHCK A         592  _____      641

D.........R...............E.....
human eEF-2K    167  ----RRVLFDDVRLQMDAKLWAE EYNRYNPPKKID IVQM                  212
C. elegans eEF-2K 151 ----RSVYFEDVQLQMEAKLWGE EDYNRHKPPKQ VDIMQM                 196
mouse eEF-2K    166  ----RELYFEEDVKMQMVCRDWGNKE NQKKPPKKIE FLMS                 211
MHCK A         642  _____      691

K...............
human eEF-2K    213  CVIEMIDVK-----GSP-LYHLEHFIEGKYIKYNSNSGFV--S-NAAARLTPQ      256
C. elegans eEF-2K 197 CIELKDRP-----GQP-LFHLEHYIEGKYIKYNSNSGFVRDDNI-RLTPQ        239
mouse eEF-2K    212  WVVELIDRS PSSNGQPI CSIEPIIVGEEKKNNSNYGAVLT-N--RSTPQ        255
MHCK A         692  _____      738
```

FIG. 5B

```
human eEF-2K    257 ................................AFSHFTFERSGHQMVVDIQGVDLYTDPQIHTVVGTDY.......... 306
C.elegans eEF-2K 240 ................................AFSHFTFERSGHQLIVVDIQGVGDLYTDPQIHTEKGTDF.......... 289
mouse eEF-2K    256 ................................AFSHFTFERSGHQMVVDIQGVGDLYTDPQIHTVVGTDY.......... 305
MHCK A          739 ..............T.................AFSHFTYELSNKQMIVVDDLYTDPQIHTPDCKGFGIGNLGKAGIN..... 788 human eEF-2K    307 .........E....A.................R...............N..K................................ 354
C.elegans eEF-2K 290 ................................LFFHSHRCNDICETMDISNFELSPPEIEATEVAMEVAAKQKKSCIVPPTV.. 339
mouse eEF-2K    306 ................................LFFYSHACNRICQSMGLTPFDLSPREQDAVNQSTRLLQSAKT--ILRGTE.. 353
MHCK A          789 ................................KEITHKCNAVCALIDL............................................ 805 human eEF-2K    355 .........V...G...................-RP........................................... 400
C.elegans eEF-2K 340 ................................FEARRNRISSECVHVEHGISMDQLRKRKTL---NQSTDLSAKSHNEDCV 386
mouse eEF-2K    354 ................................EKCGSPRIRTLSSS---RPPLL-LRLSENSGDENMSDVTFDSLPSSSA 399 human eEF-2K    401 .........S....AS....HL....E................................................G. 449
C.elegans eEF-2K 387 ................................CPECIPVVEQLCEPCSEDEEEEDYPRSEKSGNSQKSRRSRMSISTRSS 436
mouse eEF-2K    400 ................................TPHSQKLDH-IHWPVFGDLDNMGPRDHDRMDNHRDSENSGDSYPSEKRS 448 human eEF-2K    450 -E........YS..-KY....................-......K......S....... 494
C.elegans eEF-2K 437 GDESASRPRKCGFVDLNSLRQRHDSFRSSVGTYSMNSSRQTRDTEKDEFW............ 486
mouse eEF-2K    449 -DLDDPEPREHG-HSNGNR-RHESDEDSLGS-SGRVCVETWNLLNPSRL............ 493 human eEF-2K    495 .........A.................EK..............-I........... 532
C.elegans eEF-2K 487 KVLRKQSVPANILSLQQMAANLENDEDVPQVTGHQFSVLGQIHIDLSR 536
mouse eEF-2K    494 HLPRPSAVALEVQRINALDLGRKIGK---------SVLGKVHLAMVR 531
```

FIG. 5C

```
human eEF-2K    533  ...........G..YHELGRFVEVDSEHKEMLEGSENDARVPIKYDKSAIFHLDIARKCGILE  565
C.elegans eEF-2K 537  ..............YHEGGRFCEKDEE------------------WDRESAIFHLEHAADLGELE  586
mouse eEF-2K    532                                                                       564 human eEF-2K    566  ...........Q..V.AVLTSAHIVLGLPHELLKEVTVDDLFPNGFGEQENGIRADKGQKPCDLEE  596
C.elegans eEF-2K 587                                                                       636
mouse eEF-2K    565        AIVGLGLMYSQLPHHILADVSLKE-----TEENKTK--                          595 human eEF-2K    597  ...........S.Q.....L.FGSDLMEIAAEMGDKGAMLYMAHAYETGQHLGPNRTDYKKSIDWYQRVV  645
C.elegans eEF-2K 637  ..............GFDYLLKAAEAGDRHSMILVARAFDTGLNLSPDRCQDWSEALHWYNTAL  686
mouse eEF-2K    596                                                                       644 human eEF-2K    646  ...........M...R.MM...F..Y..E.D.GFQEEELDSDCKTTFSSFAPLTRHEILAKMAEMYKEGGYGLNQDFERA  689
C.elegans eEF-2K 687       ------ETTDCDEG-GEYDGIQDEPQYALLAREAEMLLTGGEGIDKNPQRS             736
mouse eEF-2K    645                                                                       688 human eEF-2K    690  ...........Q.......YGLFNEAAEAAMEAMNGKLANKYYEKAEMC----GE  725
C.elegans eEF-2K 737                                                          768
mouse eEF-2K    689       GDLYTQAAEAAMEAMKGRLANQYYEKAEEAWAQMEE                     724
```

ELONGATION FACTOR-2 KINASE (EF-2 KINASE), AND METHODS OF USE THEREFOR

FIELD OF THE INVENTION

This invention relates generally to the identification of a new superfamily of eukaryotic protein kinases and the use of one member of this superfamily, elongation factor-2 kinase (eEF-2 kinase), in assays to screen for specific inhibitors. Specific inhibitors of the eEF-2 kinase may be potent therapeutics for amelioration of malignant transformation. Additionally, sequences complementary to eEF-2 kinase may have therapeutic efficacy as antisense drugs or be used in gene therapy. Specifically, the invention relates to assays developed using the recombinant eEF-2 kinase to screen for inhibitors of phosphorylation of a peptide derived from the myosin heavy chain (MHC) protein.

BACKGROUND OF THE INVENTION

Protein phosphorylation plays a critical role in many cellular processes (Krebs (1994) *Trends Biochem. Sci.* 19:439; Hanks and Hunter, (1996) *FASEB J.* 9:576–596; Hardie and Hanks, (1995) *The Protein Kinase Facts Book* (Academic, London)). There are two well-characterized superfamilies of protein kinases, with most of the protein kinases belonging to the serine/threonine/tyrosine kinase superfamily (Hanks and Hunter, (1996); Hardie and Hanks, (1995)). The characterization of several hundred members of this superfamily revealed that they all share a similar structural organization of their catalytic domains which consist of twelve conserved subdomains (Hanks and Hunter, (1996); Hardie and Hanks, (1995)). The other superfamily is referred to as the histidine kinase superfamily and is involved in the prokaryotic two-component signal transduction system, acting as sensor components (Stock et al., (1989) *Microbiol. Rev.* 53:450–490; Parkinson and Kofoid, (1992) *Annu. Rev. Genet.* 26:71–112; Swanson, et al., (1994) *Trends Biochem. Sci.* 19:485–490). Recently, eukaryotic members of this superfamily have also been described (Chang et al., (1993) *Science* 263:539–544; Ota and Varshavsky, (1993) *Science* 262:566–569; Maeda et al., (1994) *Nature* 369:242–245). Mitochondrial protein kinases have also recently been described that show structural homology to the histidine kinases, but phosphorylate their substrates on serine (Popov et al., (1992) *J. Biol. Chem.* 267:13127–13130; Popov et al., (1993) *J. Biol. Chem.* 268:26602–22606). Finally, several new protein kinases have been reported that show a lack of homology with either of the kinase superfamilies (Maru and Witte, (1991) *Cell* 67:459–468; Beeler et al., (1994) *Mol. Cell. Biol.* 14:982–988; Dikstein et al., (1996) Cell 84:781–790; Futey et al., (1995) *J. Biol. Chem.* 270:523–529; Eichenger et al., (1996) *EMBO J.* 15:5547–5556). However, these protein kinases are viewed as an exception to the general rule as they have yet to be fully characterized.

The cloning and sequencing of the extensively characterized eukaryotic elongation factor-2 kinase (eEF-2 kinase) from a variety of eukaryotic organisms has now revealed the existence of a novel class of protein kinases (Ryazanov et al., (1997) *Proc. Natl. Acad. Sci., USA* 94:4884–4889). eEF-2 kinase, previously known as $Ca^{2+}$/calmodulin-dependent protein kinase III, is highly specific for phosphorylation of elongation factor-2 (eEF-2), an abundant cytoplasmic protein that catalyzes the movement of the ribosome along mRNA during translation in eukaryotic cells (reviewed in Ryazanov and Spirin, (1993) In *Translational Regulation of Gene Expression* (Plenum, New York) Vol. 2, pp. 433–455; Nairn and Palfrey, (1996) In *Translational Control* (CSHL Press, New York) pp. 295–318). All mammalian tissues, and various invertebrate organisms, exhibit eEF-2 kinase activity (Abdelmajid et al., (1993) *Int. J. Dev. Biol.* 37:279–290). eEF-2 kinase catalyzes the phosphorylation of eEF-2 at two highly conserved threonine residues located within a GTP-binding domain (Ryazanov and Spirin, (1993) In *Translational Regulation of Gene Expression* (Plenum, New York) Vol. 2, pp. 433–455; Nairn and Palfrey, (1996) In *Translational Control* (CSHL Press, New York) pp. 295–318). When eEF-2 is phosphorylated, it becomes inactive with respect to protein synthesis (Ryazanov et al., (1988) *Nature* 334:170–173). Since eEF-2 phosphorylation is dependent on $Ca^{2+}$ and calmodulin, eEF-2 kinase plays a pivotal role in modulating the protein synthesis rate in response to changes in intracellular calcium concentration. Phosphorylation of eEF-2 has also been linked to the regulation of cell cycle progression. For example, transient phosphorylation of eEF-2 occurs during the mitogenic stimulation of quiescent cells (Palfrey et al., (1987) *J. Biol. Chem.* 262:9785–9792) and during mitosis (Celis et al., (1990) *Proc. Natl. Acad. Sci., USA* 87:4231–4235). In addition, changes in the level of eEF-2 kinase activity is associated with a host of cellular processes such as cellular differentiation (End et al., (1982) *J. Biol. Chem.* 257:9223–9225; Koizumi et al., (1989) *FEBS Lett.* 253:55–58; Brady et al., (1990) *J. Neurochem.* 54:1034–1039), oogenesis (Severinov et al., (1990) *New Biol.* 2: 887–893), and malignant transformation (Bagaglio et al., (1993) *Cancer Res.* 53:2260–2264).

The sequence eEP-2 kinase appears to have no homology to either the $Ca^{2+}$/calmodulin-dependent protein kinases or to any members of the known protein kinase superfamilies (Ryazanov et al., (1997) *Proc. Natl. Acad. Sci., USA* 94:4884–4889). However, the recently described myosin heavy chain kinase A (MHCK A) from Dictyostelium (Futey et al., (1995) *J. Biol. Chem.* 270:523–529) shows a great deal of homology with eEF-2 kinase. These two kinases define a novel class of protein kinases that may represent a new superfamily.

Evidence for MHCK and eEF-2 kinase forming the core of a new superfamily is as follows. MHCK A from Dictyostelium, has a demonstrated role in the regulation of myosin assembly (Futey et al., (1995) *J. Biol. Chem.* 270:523–529; Côté et al., (1997) *J. Biol. Chem.* 272:6846–6849). eEF-2 kinase is a ubiquitous $Ca^{2+}$/calmodulin-dependant protein kinase involved in the regulation of protein synthesis by $Ca^{2+}$ (Redpath et al., (1996) *J. Biol. Chem* 271:17547–17554; Ryazanov et al., (1997) *Proc. Natl. Acad. Sci., USA* 94:4884–4889). Both MHCK A and eEF-2 kinase display no homology to any of the known protein kinases, but are strikingly similar to each other; amino acid sequences of their catalytic domains are 40% identical. Another protein kinase homologous to MHCK A and eEF-2 kinase has recently been identified in Dictyostelium (Clancy et al., (1997) *J. Biol. Chem.* 272:11812–11815), and an expressed sequence tag (EST) sequence, with a high degree of similarity to the catalytic domain common to both MHCK A and eEF-2 kinase, has been deposited in GenBank (clone FC-AN09/accession #C22986). An amino acid sequence alignment of the catalytic domains of these new protein kinases is shown in FIG. 1A. These kinases have a catalytic domain of approximately 200 amino acids which can be subdivided into seven conserved subdomains. Subdomains V, VI, and VII have a predicted β-sheet structure and are presumably involved in ATP-binding, while subdomains I through IV may be involved in substrate binding and catalysis. These new protein kinases have no homology to the members of the eukaryotic serine/threonine/tyrosine protein kinase superfamily with the exception of the GXGXXG motif in subdomain VI which is present in many ATP-binding proteins. Thus, MHCK A, eEF-2 kinase, and related protein kinases may represent a new superfamily. Evolutionary analysis of these new kinases (FIG. 1B) reveals that they can be subdivided into 2 families: the eEF-2 kinase family which includes eEF-2 kinases from different organisms, and the MHCK family which includes MHCK A, MHCK B and FC-AN09. These two families appear to have split more than a billion years ago.

An interesting question is why does nature employ these unusual kinases to phosphorylate eEF-2 and myosin heavy chains? Perhaps the answer is related to the secondary structure of the phosphorylation sites. As was originally reported by Small et al. (Small et al., (1977), *Biochim. Biophys. Res. Comm.* 79:341–346), phosphorylation sites are usually located at predicted β-turns. Subsequent studies, including X-ray crystallographic data, demonstrated that phosphoacceptor sites in substrates of conventional protein kinases are often located in turns or loops and usually have flexible extended conformation (Knighton et al., (1991) *Science* 253:414–420; Pinna and Ruzzene (1996) *Biochim. Biophys. Acta* 1314:191–225). In contrast to this, the existing evidence suggests that the peptides around phosphorylation sites for eEF-2 kinases and MHCK A have an α-helical conformation. The two major phosphorylation sites for MHCK A are located in a region which has a coiled-coil α-helical structure (Vaillancourt et al., (1988) *J. Biol. Chem.* 253:10082–10087). The major phosphorylation site in eEF-2, threonine 56, is located within a sequence which is homologous among all translational elongation factors. In the crystal structure of the prokaryotic elongation factor EF-Tu, this sequence has an α-helical conformation (Polekhina et al., (1996) *Structure* 4:1141–1151; Abel et al., (1996) *Structure* 4:1153–1159). These facts suggest that eEF-2 kinase and MHCK A differ from conventional protein kinases in that they phosphorylate amino acids located within α-helices.

Thus, in addition to the two well-characterized superfamily of eukaryotic protein kinases, which phosphorylate amino acids located in loops and turns, there appears to be a third superfamily of α-helix-directed kinases.

SUMMARY OF THE INVENTION

Novel protein kinase inhibitors have the potential to form the basis for pharmaceutical compositions that can ameliorate malignant transformation. In order to find these inhibitors, libraries of chemical compounds are routinely screened using an automated protein kinase assay. The drawback to this approach is that most protein kinases have a very similar structure, thus making it difficult to specific inhibitors which act solely on a particular protein kinase. We have recently determined the primary structure of eEF-2 kinase, a ubiquitous enzyme which is involved in the regulation of protein synthesis and the cell cycle. Unexpectedly, we found that eEF-2 kinase has a unique structure. It has no homology to any other mammalian protein kinase. This feature makes eEF-2 kinase an ideal target in the search for a specific protein kinase inhibitor. Since preliminary evidence suggests that eEF-2 kinase is upregulated in human cancers (data not shown), including, but not limited to, breast cancer, identification of specific inhibitors of eEF-2 kinase can eventually lead to the development of novel anticancer drugs. In order be able to perform a high through-put screen for an eEF-2 kinase inhibitor, it is first necessary to develop a simple assay which is amenable to automation. The existing assay involves incubation of partially purified eEF-2 kinase along with purified eEF-2 and $[\gamma\text{-}^{32}P]ATP$ as substrates in the presence of increasing concentrations of candidate inhibitors. Results are then obtained by electrophoretic separation of the reaction mixtures, followed by autoradiography. Results are then quantified by either densitometry or scintillation counting of excised bands from the gel containing $^{32}P$-eEF-2. Clearly, this assay, as it stands, is time-consuming, expensive, and not amenable to automation. Furthermore, it is difficult to purify large amounts of native eEF-2 required to perform multiple assays, and attempts to overexpress a recombinant form of eEF-2 were unsuccessful as its overexpression was toxic to host strains (personal communication from James Bodley, University of Minnesota, Minn.). Therefore, we have developed new methodologies for determining eEF-2 kinase activity, which involves the use of a specific peptide substrate; easily and economically manufactured in large scale. These methods are relatively inexpensive, fast, and can be fully automated.

In our first attempt to use a peptide as an eEF-2 kinase substrate, we generated peptides centered around the phosphorylation site of eEF-2. This strategy did not yield a peptide that was functional in phosphorylation assays (data not shown). Surprisingly, we found that a 16' mer peptide (RKKFGESEKTKTKEFL (SEQ ID NO: 20)), based on the phosphorylation site of Dictyostelium discoideum MHC, was an acceptable substrate for use with eEF-2 kinase in phosphorylation assays. It is interesting to note that while eEF-2 kinase can phosphorylate a peptide derived from MHC, it is not able to phosphorylate native MHC (Ryazanov et al., (1997) *Proc. Natl. Acad. Sci., USA* 94:4884–4889).

In accordance with the present invention, a new superfamily of protein kinases and corresponding methods for assaying their phosphorylation activity are disclosed. The protein kinases of this new superfamily have the following characteristics: 1) No significant sequence homology to protein kinases of either the serine/threonine/tyrosine kinase or histidine kinase super families; 2) moderate to high ($\geq 40\%$) to eEF-2 kinases from any organism; and, 3) phosphorylates an amino acid within an α-helical domain.

The present invention also relates to a recombinant DNA molecule or cloned gene, or a degenerate variant thereof, which encodes eEF-2 kinase; preferably a nucleic acid molecule, in particular a recombinant DNA molecule or cloned gene, encoding the eEF-2 kinase has a nucleotide sequence or is complementary to a DNA sequence shown in FIG. 5 (SEQ ID NO: 1, 3, and 9).

The human and murine DNA sequences of the eEF-2 kinase gene of the present invention or portions thereof, may be prepared as probes to screen for complementary sequences and genomic clones in the same or alternate species. The present invention extends to probes so prepared that may be provided for screening cDNA and genomic libraries for the eEF-2 kinase gene. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences set forth in FIG. 5 (SEQ ID NO: 1, 3, and 9). Correspondingly, the preparation of antisense RNA and ribozymes are included herein.

The present invention also includes eEF-2 kinase proteins having the activities noted herein, and that display the amino acid sequences set forth and described above and selected from SEQ ID NO: 2, 4, and 10.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding eEF-2 kinase, and more particularly, the complete DNA sequence determined from the sequences set forth above and in SEQ ID NO: 1, 3, and 9.

According to other preferred features of certain preferred embodiments of the present invention, a recombinant expression system is provided to produce biologically active animal or human eEF-2 kinase.

The present invention naturally contemplates several means for preparation of eEF-2 kinase, including as illustrated herein known recombinant techniques, and the invention is accordingly intended to cover such synthetic preparations within its scope. The isolation of the cDNA and amino acid sequences disclosed herein facilitates the production of eEF-2 kinase by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective at attenuating eEF-2 kinase activity of target mammalian cells by interrupting or potentiating the phosphorylation of eEF-2. In one instance, the test drug could be administered to a cellular sample along with ATP carrying a detectable label on its γ-phosphate that gets transferred to eEF-2, or a peptide substrate, by eEF-2 kinase. Quantification of the labeled eEF-2 or peptide substrate is diagnostic of the candidate drug's efficacy. A further embodiment would provide for the assay to be performed using a purely in vitro system comprised of eEF-2 kinase, ATP or labeled ATP, eEF-2 or peptide analog of a portion of eEF-2 or MHC, appropriate buffer, and detection reagents and/or instrumentation to detect and quantify the extent of eEF-2 kinase-directed phosphorylation activity.

The assay system could more importantly be adapted to identify drugs or other entities that are capable of binding to the eEF-2 kinase and/or its cognate phosphorylation target (e.g. eEF-2), either in the cytoplasm or in the nucleus, thereby inhibiting or potentiating eEF-2 kinase activity and its resultant phenotypic outcome. Such an assay would be useful in the development of drugs that would be specific against particular cellular activity, or that would potentiate such activity, in time or in level of activity. For example, such drugs might be used to treat various carcinomas or other hyperproliferitive pathologies.

The present invention likewise extends to antibodies against specifically phosphorylated eEF-2 kinase targets (e.g. eEF-2 or peptide), including naturally raised and recombinantly prepared antibodies. These antibodies and there labeled counterparts are included within the scope of the present invention for their particular ability in detecting eEF-2 kinase activity via detection of the phosphorylated product by ELISA or any other immunoassay known to the skilled artisan.

In the instance where a radioactive label, such as the isotopes $^{3}H$, $^{14}C$, $^{32}P$, $^{33}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

In a further embodiment, the present invention contemplates antagonists of the activity of eEF-2 kinase. In particular, an agent or molecule that inhibits phosphorylation of eEF-2. In a specific embodiment, the antagonist can be a peptide comprising sequences, or sequence variants adjacent to, and including, the phosphorylation site in either eEF-2 or MHC. It is anticipated that these peptides would be competitive inhibitors of eEF-2 kinase's cognate target. In still a further embodiment, the invention contemplates antisense drugs such that sequences complementary to the eEF-2 kinase mRNA inhibit production of functional eEF-2 kinase. In a specific embodiment, the antisense drug may be a complementary oligonucleotide (DNA, RNA, or hybrid thereof), which may or may not be modified so as to have the following characteristics: 1) enhanced hybridization kinetics; 2) tighter binding to complementary sequence than its unmodified counterpart; and/or, 3) resistance to nucleases. In another specific embodiment, the antisense drug may be a complementary oligonucleotide (DNA, RNA, or hybrid thereof), that has the ability to cleave its target sequence either by ribozyme, or ribozyme-like, activity, or by nuclease activity imparted on the antisense drug by physical attachment to anyone of a number of nucleases.

More specifically, the therapeutic method generally referred to herein could include the method for the treatment of various pathologies or other cellular dysfunctions and derangements by the administration of pharmaceutical compositions that may comprise effective inhibitors of eEF-2 kinase activity, or other equally effective drugs developed for instance by a drug screening assay prepared and used in accordance with a further aspect of the present invention.

Accordingly, it is a principal object of the present invention to provide a method and an associated assay system for screening potential inhibitors of eEF-2 kinase activity.

It is a further object of the present invention to provide antibodies to the phosphorylated eEF-2 kinase target, and methods for their preparation, including recombinant means.

It is a further object of the present invention to provide a method for detecting eEF-2 kinase activity in mammals in which invasive, spontaneous, or idiopathic pathological states are suspected to be present.

It is a still further object of the present invention to provide a method for the treatment of mammals to control the amount or activity of eEF-2 kinase, so as to alter the adverse consequences of such presence or activity, or where beneficial, to enhance such activity.

It is a still further object of the present invention to provide a method for the treatment of mammals to control the amount or activity of eEF-2 kinase, so as to treat or avert the adverse consequences of invasive, spontaneous or idiopathic pathological states.

It is a still further object of the present invention to provide pharmaceutical compositions for use in therapeutic methods which comprise or are based upon a sequence complementary to that of the eEF-2 kinase mRNA, which would form the basis for an antisense therapeutic that can reduce expression, and thus activity, of eEF-2 kinase.

It is yet another object of the invention to provide pharmaceutical compositions for use in therapeutic methods which comprise or are based upon peptide analogs of eEF-2 phosphorylation target amino acid sequences. It is anticipated that certain peptide analogs may act as efficacious competitive inhibitors of eEF-2 phosphorylation.

Other objects and advantages will become apparent to those skilled in the art from a review of the ensuing description which proceeds with reference to the following illustrative drawings.

BRIEF DESCRIPTION OF THE DRAWINGS

FIG. 5. Sequence alignment of *C. elegans*, mouse, human eEF-2 kinase, and the catalytic domain of *Dictyostelium discoideum* MHCK A. Identical amino acids are indicated by dark blue boxed regions and chemically conserved amino acids are indicated by light blue shaded regions. Amino acids in the human sequence that are identical to the mouse sequence are represented by dots. Amino acids underlined in black correspond to the six regions that match peptides obtained from the sequencing of purified rabbit reticulocyte eEF-2 kinase. The GXGXXG nucleotide-binding motif is underlined in red. The blue dashed line over residues 625–632 in *C. elegans* eEF-2 kinases designates the amino acids corresponding to exon 4, which is missing in Cefk-2.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

Figure 1B:
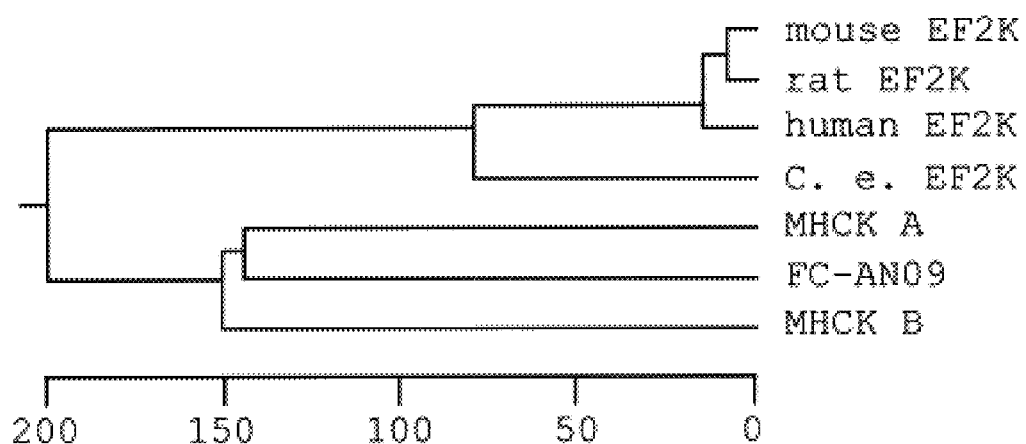
FIG. 1. A, Sequence alignment of the catalytic domains of human eEF-2 kinase, *C. elegans* eEF-2 kinase, MHCK A, MHCK B and clone FC-ANO9. Identical amino acids (bold) and conserved hydrophobic amino acids (°) are noted. B, Phylogenetic tree of sequences shown in (A), with the addition of mouse and rat eEF-2 kinases. Tree was obtained using the J. Hein method with PAM250 residue weight table. The following accession numbers were used for the sequences: U93846-U93850, 1495779, 1170675, 1903458, C22986.

The terms "elongation factor-2 kinase", "eEF-2 kinase ", "EF-2 kinase", "Cefk", and any variants not specifically listed, may be used herein interchangeably, and as used throughout the present application and claims refer to proteinaceous material including single or multiple proteins, and extends to those proteins having the amino acid sequence data described herein and presented in FIGS. 1 and 5 (SEQ ID NO: 2, 4, 6, 8, 10, 12, abd 14), and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms elongation factor-2 kinase", "eEF-2 kinase", "EF-2 kinase", and "Cefk" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired fractional property of immunoglobulin-binding is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the –10 and –35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding eEF-2 kinase which code for a protein having the same amino acid sequence as SEQ ID NO: 2, 4, and 10, but which are degenerate to SEQ ID NO: 1, 3, and 9. By "degenerate to" is meant that a different three-letter codon is used to specify a particular amino acid. It is well known in the art that the following codons can be used interchangeably to code for each specific amino acid:

```
Phenylalanine (Phe or F)  UUU or UUC

Leucine (Leu or L)        UUA or UUG or CUU or CUC or CUA or CUG

Isoleucine (Ile or I)     AUU or AUC or AUA

Methionine (Met or M)     AUG

Valine (Val or V)         GUU or GUC of GUA or GUG

Serine (Ser or S)         UCU or UCC or UCA or UCG or AGU or AGC

Proline (Pro or P)        CCU or CCC or CCA or CCG

Threonine (Thr or T)      ACU or ACC or ACA or ACG

Alanine (Ala or A)        GCU or GCG or GCA or GCG

Tyrosine (Tyr or Y)       UAU or UAC

Histidine (His or H)      CAU or CAC

Glutamine (Gln or Q)      CAA or CAG

Asparagine (Asn or N)     AAU or AAC

Lysine (Lys or K)         AAA or AAG

Aspartic Acid (Asp or D)  GAU or GAC

Glutamic Acid (Glu or E)  GAA or GAG

Cysteine (Cys or C)       UGU or UGC

Arginine (Arg or R)       CGU or CGC or CGA or CGG or AGA or AGG

Glycine (Gly or G)        GGU or GGC or GGA or GGG

Tryptophan (Trp or W)     UGG

Termination codon         UAA (ochre) or UAG (amber) or UGA (opal)
```

It should be understood that the codons specified above are for RNA sequences. The corresponding codons for DNA have a T substituted for U.

Mutations can be made in SEQ ID NO: 1, 3, and 9 such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

---

Amino acids with nonpolar R groups

Alanine
Valine
Leucine
Isoleucine
Proline
Phenylalanine
Tryptophan
Methionine
Amino acids with uncharged polar R groups Glycine
Serine
Threonine
Cysteine
Tyrosine
Asparagine
Glutamine
Amino acids with charged polar R groups (negatively charged at pH 6.0)

Aspartic acid
Glutamic acid
Basic amino acids (positively charged at pH 6.0)

Lysine
Arginine
Histidine (at pH 6.0)

---

Another grouping may be those amino acids with phenyl groups:

Phenylalanine

Tryptophan

Tyrosine

Another grouping may be according to molecular weight (i.e., size of R groups):

| | |
|---|---|
| Glycine | 75 |
| Alanine | 89 |
| Serine | 105 |
| Proline | 115 |

-continued

| | |
|---|---|
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10–20° C. below the predicted or determined T$_m$ with washes of higher stringency, if desired.

In one aspect, the present invention relates to the identification of a new superfamily of protein kinases centered around eEF-2 kinase. Accordingly, it includes the DNA sequences coding for these family members. In addition, the invention also contemplates that each member of this new protein kinase superfamily has its own cognate phosphorylation target. As specified supra, two of these targets are eEF-2 and MHC, which are phosphorylated by eEF-2 kinase and MHCK A, respectively.

In a particular embodiment, the present invention relates to phosphorylation target analogs, which are short peptide sequences derived from phosphorylation targets of this new superfamily of protein kinases centered around eEF-2 kinase. Specifically, it is contemplated that these peptide analogs will be instrumental in the development of high throughput screening assays to identify inhibitors of members of this new superfamily.

As overexpression of eEF-2 kinase has been associated with a variety of cancers and other hyperproliferitive pathologies (discussed supra), the invention also includes assay systems for the screening of potential drugs effective at inhibiting eEF-2 kinase activity. It is contemplated that any of the recited assays can be automated using technology that is standard to the skilled artisan.

As stated above, the present invention also relates to a recombinant DNA molecule or cloned gene, or a degenerate variant thereof, which encodes a eEF-2 kinase, or a fragment thereof, that possesses a molecular weight of about 100 kD and an amino acid sequence set forth in FIG. 5 (SEQ ID NO: 2, 4, and 10); preferably a nucleic acid molecule, in particular a recombinant DNA molecule or cloned gene, encoding the 100 kD eEF-2 kinase has a nucleotide sequence or is complementary to a DNA sequence shown in FIG. 5 (SEQ ID NO: 1, 3, and 9).

Therapeutic possibilities are raised by the knowledge of the eEF-2 kinase sequence and the existence of peptide analogs that can act as phosphorylation targets for the kinase. Accordingly, it is contemplated that sequences that are derived from the complement to the eEF-2 kinase mRNA sequence, and various modifications thereof, can act as potent antisense drugs that either inhibit expression in a competitive fashion, or, more effectively, by nuclease activity associated with the antisense drug that cleaves the eEF-2 kinase mRNA sequence, thus rendering it irreversibly inactive. Alternative therapeutics are also contemplated that concern the use of peptides and peptide analogs representing portions of phosphorylation target amino acid sequences. It is envisioned that such peptide-based drugs would inhibit eEF-2 kinase activity on its native target, thus bypassing the cascade of events that would lead to malignant transformation.

The antisense or peptide-based drugs may be prepared in pharmaceutical compositions, with a suitable carrier and at a strength effective for administration by various means to a patient experiencing an adverse medical condition associated with specific malignancies for the treatment thereof. A variety of administrative techniques may be utilized, among them parenteral techniques such as subcutaneous, intravenous and intraperitoneal injections, catheterizations and the like. Average quantities of the antisense or peptide-based drugs may vary and in particular should be based upon the recommendations and prescription of a qualified physician or veterinarian.

Also, antibodies including both polyclonal and monoclonal antibodies, and drugs that modulate the production or activity of eEF-2 kinase may possess certain diagnostic applications and may, for example, be utilized for the purpose of detecting and/or measuring levels of eEF-2 kinase. It is anticipated that further experimentation will reveal a prognostic correlation between eEF-2 kinase levels and the prediction and or progression of certain malignancies associated with carcinoma. For example, eEF-2 kinase may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity of eEF-2 kinase of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against eEF-2 kinase peptides can be screened for various properties; i.e., isotype, epitope, affinity, etc. Of particular interest are monoclonal antibodies that neutralize the activity of eEF-2 kinase. Such monoclonals can be readily identified in eEF-2 kinase activity assays. High affinity antibodies are also useful when immunoaffinity purification of native or recombinant eEF-2 kinase is desired.

Preferably, the anti-eEF-2 kinase antibody used in the diagnostic methods of this invention is an affinity purified polyclonal antibody. More preferably, the antibody is a monoclonal antibody (mAb). In addition, it is preferable for the anti-eEF-2 kinase antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to eEF-2 kinase, such as an anti-eEF-2 kinase antibody, preferably an affinity-purified polyclonal antibody, and more preferably a mAb. In addition, it is preferable for the anti-eEF-2 kinase antibody molecules used herein be in the form of Fab, Fab', F(ab')$_2$ or F(v) portions or whole antibody molecules. As previously discussed, patients capable of benefiting from this method include those suffering from cancer, a pre-cancerous lesion, a viral infection or other like pathological derangement. Methods for isolating the eEF-2 kinase and inducing anti-eEF-2 kinase antibodies and for determining and optimizing the ability of anti-eEF-2 kinase antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present eEF-2 kinase and their ability to inhibit specified eEF-2 kinase activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mM glutamine, and 20% fetal calf serum. An exemplary inbred mouse strain is the Balb/c.

Methods for producing monoclonal anti-eEF-2 kinase antibodies are also well-known in the art. See Niman et al., *Proc. Natl. Acad. Sci. USA*, 80:4949–4953 (1983). Typically, the present eEF-2 kinase or a peptide analog is used either alone or conjugated to an immunogenic carrier, as the immunogen in the before described procedure for producing anti-eEF-2 kianse monoclonal antibodies. The hybridomas are screened for the ability to produce an antibody that immunoreacts with the eEF-2 kinase peptide analog and the present eEF-2 kinase.

The present invention further contemplates therapeutic compositions useful in practicing the therapeutic methods of this invention. A subject therapeutic composition includes, in admixture, a pharmaceutically acceptable excipient (carrier) and one or more of an anti-eEF-2 kinase antibody, peptide analog capable of competing for phosphorylation of eEF-2 by eEF-2 kinase, antisense drug against eEF-2 kinase mRNA, or any other compound that is found to inhibit eEF-2 kinase activity. In a preferred embodiment, the composition comprises an antigen capable of modulating the activity of eEF-2 kinase within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of eEF-2 kinase activity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

| Formulations | |
|---|---|
| Ingredient | mg/ml |
| Intravenous Formulation I | |
| cefotaxime | 250.0 |
| antibody, peptide, antisense drug, or other compound | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| ampicillin | 250.0 |
| antibody, peptide, antisense drug, or other compound | 10.0 |
| sodium bisulfite USP | 3.2 |
| disodium edetate USP | 0.1 |
| water for injection q.s.a.d. | 1.0 ml |
| Intravenous Formulation III | |
| gentamicin (charged as sulfate) | 40.0 |
| antibody, peptide, antisense drug, or other compound | 10.0 |
| sodium bisulfite USP | 3.2 |
| disodium edetate USP | 0.1 |
| water for injection q.s.a.d. | 1.0 ml |
| Intravenous Formulation IV | |
| antibody, peptide, antisense drug, or other compound | 10.0 |
| dextrose USP | 45.0 |
| sodium bisulfite USP | 3.2 |
| edetate disodium USP | 0.1 |
| water for injection q.s.a.d. | 1.0 ml |

As used herein, "pg" means picogram, "ng" means nanogram, "ug" or "$\mu$g" mean microgram, "mg" means milligram, "ul" or "$\mu$l" mean microliter, "ml" means milliliter, "l" means liter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAS, e.g., the numerous derivatives of phage $\lambda$, e.g., NM989, and other phage DNA, e.g., M13 and filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage $\lambda$, the control regions of fd coat protein, the promoter for 3-phosphoglycerate kinase or other glycolytic enzymes, the promoters of acid phosphatase (e.g., Pho5), the promoters of the yeast a-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors, a person skilled in the art will be able to construct a variety of vector/expression control sequence/host combinations that will express the DNA sequences of this invention on fermentation or in large scale animal culture.

The present invention extends to the preparation of antisense oligonucleotides and ribozymes that may be used to interfere with the expression of the eEF-2 kinase gene at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into eEF-2 kinase-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for eEF-2 kinase.

The present invention also relates to a variety of diagnostic applications, including methods for detecting and quantifying the levels of eEF-2 kinase. As mentioned earlier, eEF-2 kinase can be used to produce antibodies to itself by a variety of known techniques, and such antibodies could then be isolated and utilized as in tests for the presence and levels of eEF-2 kinase activity in suspect target cells.

As described in detail above, antibody(ies) to eEF-2 kinase can be produced and isolated by standard methods including the well known hybridoma techniques. For convenience, the antibody(ies) to eEF-2 kinase will be referred to herein as $Ab_1$ and antibody(ies) raised in another species as $Ab_2$.

The presence and levels of eEF-2 kinase in cells can be ascertained by the usual immunological procedures applicable to such determinations. A number of useful procedures are known. Three such procedures which are especially useful, utilize either eEF-2 kinase labeled with a detectable label, antibody $Ab_1$ labeled with a detectable label, or antibody $Ab_2$ labeled with a detectable label. The procedures may be summarized by the following equations wherein the asterisk indicates that the particle is labeled, and "~" stands for eEF-2 kinase:

A. $\tilde{\ }^*+Ab_1=\tilde{\ }^*Ab_1$
B. $\tilde{\ }+Ab^*=\tilde{\ }Ab_1^*$
C. $\tilde{\ }+Ab_1+Ab_2^*=\tilde{\ }Ab_1Ab_2^*$ The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, eEF-2 kinase forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-eEF-2 kinase antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

eEF-2 kinase can also be labeled with a radioactive element or with an enzyme. The radioactive label can be detected by any of the currently available counting procedures. The preferred isotope may be selected from $^3H$, $^{14}C$, $^{32}P$, $^{33}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the eEF-2 kinase may be radiolabeled and combined, for example, with antibodies or other inhibitors thereto, after which binding studies would be carried out. Solutions would then be prepared that contain various quantities of labeled and unlabeled uncombined eEF-2 kinase, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

In accordance with the above, an assay system for screening potential drugs effective to modulate the activity of eEF-2 kinase may be prepared. The eEF-2 kinase may be introduced into a test system, and the prospective drug may also be introduced into the resulting cell culture, and the culture thereafter examined to observe any changes in the eEF-2 kinase activity of the cells, due either to the addition of the prospective drug alone, or due to the effect of added quantities of the known eEF-2 kinase. Alternatively, these assays can be carried out in a purely in vitro fashion as discussed below.

PRELIMINARY CONSIDERATIONS

The following examples are presented in order to more fully illustrate the preferred embodiments of the invention. They should in no way be construed, however, as limiting the broad scope of the invention.

EXAMPLE 1

Peptide Sequencing eEF-2 kinase from rabbit reticulocyte lysate was purified as described (Hait et al., (1996) *FEBS Lett.* 397:55–60). Peptides were generated from the nitrocellulose-bound 103-kDa eEF-2 kinase protein by in situ tryptic digestion (Erdjument-Bromage et al., (1994) *Protein Sci.* 3:2435–2446) and fractionated by reverse-phase HPLC (Elicone et al., (1994) *J. Chromatogr.* 676:121–137) using a 1.0 mm Reliasil C18 column. Selected peak fraction were then analyzed by a combination of automated Edman sequencing and matrix-assisted laser-desorption time-of-flight mass spectrometry (Erdjument-Bromage et al., (1994)). The peptide sequences provided an essential lead into the cloning of eEF-2 kinase from human, mouse, rat, and *Caenorhabditis elegans*.

EXAMPLE 2

Molecular Cloning of cDNAs Encoding *C. elegans*, Mouse, Rat, and Human eEF-2 Kinases To clone the cDNA for *C. elegans* eEF-2 kinase, oligonucleotide primers were designed based on the amino and carboxy termini of the predicted gene product from F42A10.4. Reverse transcriptase-PCR (RT-PCR) was performed using these primers and total RNA from *C. elegans* (a gift form Monica Driscoll, Rutgers University). A single PCR product of ~2.3 kb was obtained and gel-purified using a gel extraction kit (Qiagen, Chatsworth, Calif.). The fragment was ligated into vector pCR2. 1 using the TA cloning kit (Invitrogen, Sorrento Valley, Calif.), and then transformed into *Escherichia coli*. Plasmid DNA was purified, and restriction analysis used to verify the orientation of the coding sequence with respect to the T7 promoter. Two clones (Cefk-1 and Cefk-2, *C. elegans* eEF-2 kinase isoforms 1 and 2) were chosen and sequenced using a Li-Cor (Lincoln, Nebr.) Long Read IR model 400L Automated DNA Sequencer. Analysis revealed that the two clones were identical except for a deletion of 24 bp in Cefk-2 which corresponds to exon 4 and probably represents an alternatively spliced form.

To clone the mouse eEF-2 kinase, degenerate primers were designed based on the amino acid sequence of two peptides from rabbit eEF-2 kinase (LTPQAFSHFTFER (SEQ ID NO: 21) and LANXYYEKAE (SEQ ID NO: 22)): primer A, CA(G/A)GC(C/G/T/A)TT(C/T)(T/A)(C/G)(T/CCA(C/T)TT(C/T)AC(C/G/T/A)TT (C/T)GA(G/A/C/A)G (SEQ ID NO: 23); and primer B, TC(C/G/T/A)GC(C/T)TT (C/T)TC(G/A)TA(G/A)TA(C/T)TT(G/A)TT(C/G/A/T)G C (SEQ ID NO: 24). RT-PCR was performed using primers A and B and poly(A)$^+$ RNA from mouse spleen (CLONTECH). A single PCR product (~1.6 kb) was cloned into pCR2.1 (Invitrogen) and sequenced. Using sequence information form these mouse eEF-2 kinase cDNA fragments, new primers were designed for 5' rapid amplification of cDNA ends (RACE) and 3' RACE to obtain full-length mouse eEF-2 kinase cDNA. 5' RACE and 3' RACE were performed using Marathon-Ready mouse spleen cDNA (CLONTECH). This was carried out according to the manufacturer's instructions using the primers AP1 and C (TACAATCAGCTGATGACCAGAACGCTC) (SEQ ID NO: 25) 5' antisense, or D (GGATTTGGACTGGACAAGAACCCCC) (SEQ ID NO: 19) 3' sense.

To clone rat eEF-2 kinases, PCR was performed on a rat PC12 cDNA library cloned in λGT10 (CLONTECH) using primer B and vector primers. A 700-bp fragment was specifically amplified. The fragment was cloned into pCR2.1 (Invitrogen) and sequenced. This 700-bp fragments was radiolabeled and used to probe the same PC12 cDNA library (600,000 plaques). Fourteen positives were obtained in the initial screening. Five plaques were chosen for further analysis and sequencing based on insert sizes that ranged from 1.4 to 2.0 kb.

Recently, eEF-2 kinase from rabbit reticulocyte lysate was purified to near homogeneity (Hait et al., (1996)). This enabled determination of its partial amino acid sequence (see EXAMPLE 1). Two peptide sequences (LTPQAFSHFTFER and LANXYYEKAE) were compared with entries in a nonredundant database using the National Center for Biotechnology Information BLAST program (Altschul et al., (1990) *J. Mol. Biol.* 215:403–410). Matches were found with a *C. elegans* hypothetical protein (F42A10.4; GenBank accession number U10414). This sequence was obtained from the *C. elegans* genome sequencing project and is located on chromosome III (Wilson et al., (1994) *Nature* 368:32–38). The 100% identity between the sequenced peptides and the *C. elegans* protein, as well as the fact that the predicted molecular weight of the *C. elegans* protein is similar to that of eEF-2 kinase, suggested that this gene encoded eEF-2 kinase. We cloned the full-length cDNA by RT-PCR using *C. elegans* total RNA. Several clones were isolated and sequenced. Cefk-1 has six of the predicted exons and encodes 768 amino acids. Cefk-2 represents an alternatively spliced form that has five exons; it is missing amino acids 625–632 that correspond to exon four.

As is demonstrated in EXAMPLE 3, Cefk-1 and Cefk-2 have eEF-2 kinase activity when expressed in cell-free system using a wheat germ extract coupled transcription/translation system.

Figure 2:
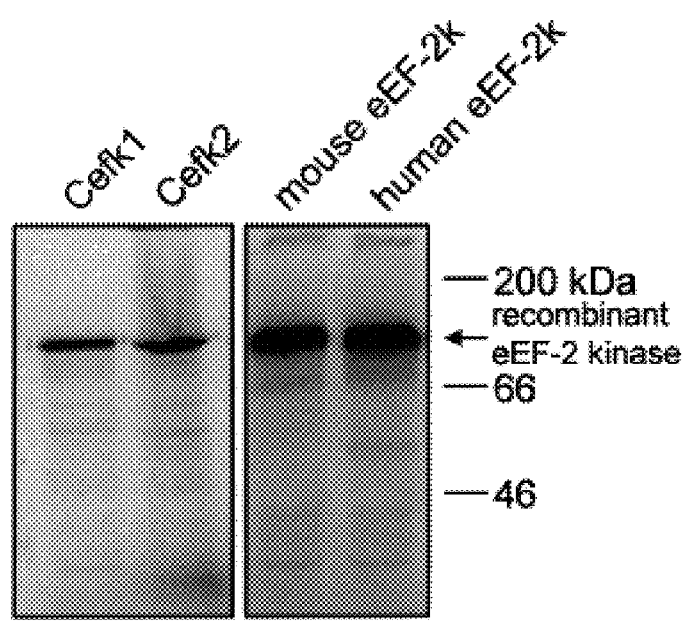
FIG. 2. Expression of recombinant eEF-2 kinase in vitro. Plasmid DNA from clones Cefk-1, Cefk-2, as well as mouse and human eEF-2 kinase cDNA were used in the TNT wheat germ extract coupled transcription/translation system (Promega). [$^{35}$S]Methionine-labeled products were then analyzed by SDS/PAGE.

To determine the amino acid sequence of mammalian eEF-2 kinase, we cloned and sequenced the cDNA of mouse eEF-2 kinase. We reasoned that since the sequenced peptides from rabbit eEF-2 were 100% identical to *C. elegans* eEF-2 kinase, then the two peptides should also match the sequence of mouse eEF-2 kinase. Degenerate primers were designed based on the amino acid sequence of the peptides and were used to perform RT-PCR on mouse spleen poly(A)$^+$ mRNA. A single PCR product of ~1.6 kb was obtained and sequenced. To obtain the full-length cDNA, 5' RACE and 3' RACE were performed using mouse spleen cDNA. The full-length cDNA, which encodes 724 amino acids, was expressed in a cell-free coupled transcription/translation system. A single translation product with an apparent molecular weight of 100 kDa was obtained (FIG. 2).

We next cloned and sequenced cDNA for rat eEF-2 kinase using a fragment of mouse eEF-2 kinase cDNA to probe a PC12 cDNA library. However, after this work was completed, a paper describing the cloning of eEF-2 from rat skeletal muscle was published (Redpath et al., (1996) *J. Biol. Chem.* 271:17547–17554) and the reported sequence appears to be identical to the eEP-2 kinase sequence from PC12 cells. Like the mouse eEF-2 kinase, the rat eEF-2 kinase cDNA encodes a 724-amino acid protein.

We also cloned the human eEF-2 kinase cDNA. RT-PCR was performed on poly(A)$^+$ mRNA from the human glioma cell line T98G using 20' mer primers corresponding to the 5' and 3' ends of the mouse eEF-2 kinase coding region. The human eEF-2 kinase cDNA encodes a 725 amino acid protein.

EXAMPLE 3

Expression of eEF-2 Kinase From *C. elegans*, Mouse, Rat, and Human in a Cell-Free System Plasmid DNA from clones Cefk-1, Cefk-2, as well as mouse and human eEF-2 kinase cDNA were used in the TNT wheat germ extract coupled transcription/translation system (Promega). [$^{35}$S]Methionine-labeled products were then analyzed by SDS/PAGE. The reaction mixture (50 μl total volume) contained 1 μg of plasmid DNA and 26 μCi of [$^{35}$S]methionine (specific activity=1175.0 Ci/mmol; 1 Ci=37 GBq). Other components were added to the reaction mixture according to the manufacturer's protocol. The reaction mixture was incubated for 1.5 h at 30° C. and terminated by incubation on ice. A 10 μl aliquot of the reaction mixture was mixed with 2 μl of 5×Laemmli buffer and boiled for 5 min. Samples were analyzed by SDS/PAGE on 8% gels and autoradiography.

The remainder of the transcription/translation reaction was diluted 4-fold with buffer A (20 mM Tris-HCl, pH 7.4/1 MM MgCl$_2$/10% glycerol/7 mM 2-mercaptoethanol) and applied to a HR5/5 Mono Q column (Pharmacia) equilibrated with buffer A. The column was developed with 20 column volumes of a 50–600 mM KCl linear gradient to buffer A.

To assay for eEF-2 kinase activity, 5 μl from each fraction was added to a reaction mixture (40 μl) containing 50 mM Hepes-KOH (ph. 7.4) 10 mM magnesium acetate, 0.1 mM CaCl$_2$, 5 mM dithiothreitol, 50 μM ATP, 2 μCi [γ-$^{32}$P]ATP, 0.6 μg calmodulin, and 0.5 μg rabbit reticulocyte eEF-2. Reactions were incubated at 30° C. for 2 min and were terminated by adding 20 μl of 3×Laemmli sample buffer. Samples were boiled for 5 min and proteins separated by SDS/PAGE on 8% gels. Phosphoproteins were analyzed by autoradiography.

Figure 3A:
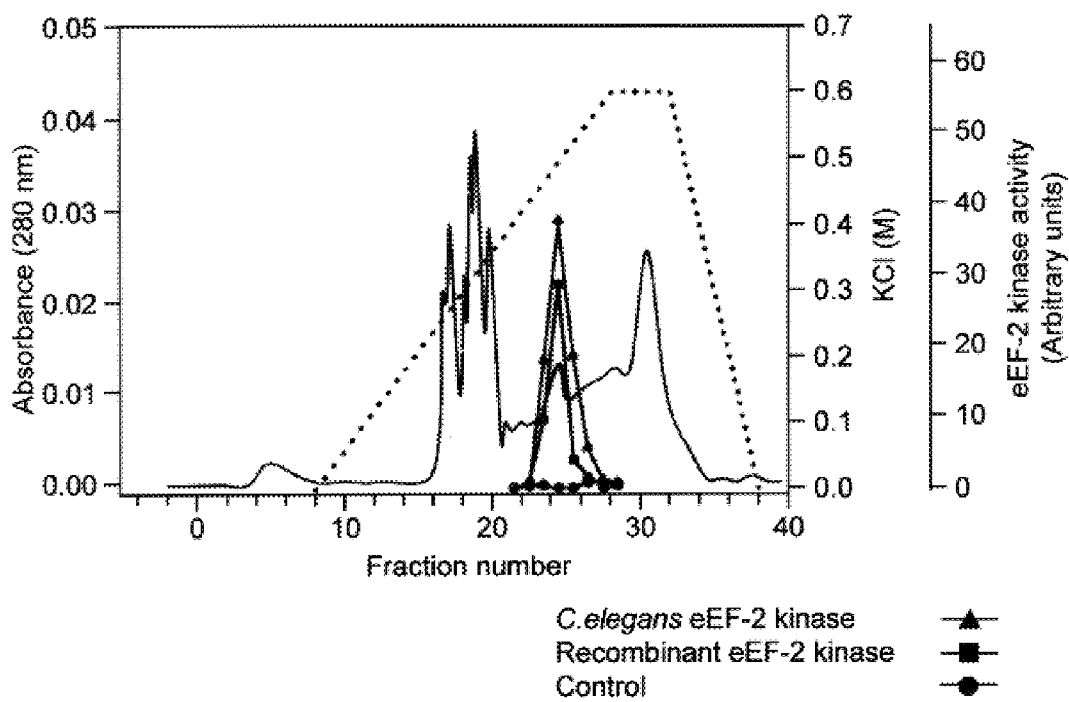
FIG. 3. Activity of recombinant eEF-2 kinase in vitro. A large scale (0.5 ml) reaction using a mixture of Cefk-1 and Cefk-2 plasmids was run as in FIG. 2, with the omission of labeled methionine. In the control experiment, the reaction was run with a plasmid containing a luciferase gene. (A) The reaction mixtures were separated by chromatography on a Mono Q column as described. (B) eEF-2 kinase activity in fractions was measured as the ability to phosphorylate purified rabbit eEF-2 in the presence of [γ-$^{32}$P]ATP. Purified rabbit reticulocyte eEF-2 kinase was used in the (+) control experiments. (C) $Ca^{2+}$/calmodulin-dependency of recombinant *C. elegans* eEF-2 kinase. Mono Q fraction 25 was assayed in a standard eEF-2 kinase assay in the presence and absence of $Ca^{2+}$ and calmodulin and 20 µM trifluoperazine (TFP) or N-(6 aminohexyl)-5-chloro-1-napthalene-sulfonamide (W7). (D) $Ca^{2+}$/calmodulin-dependency of recombinant human eEF-2 kinase. Human eEF-2 kinase cDNA was expressed in a coupled transcription/translation system as described above and eEF-2 kinase activity was assayed without further purification.
Figure 3B:
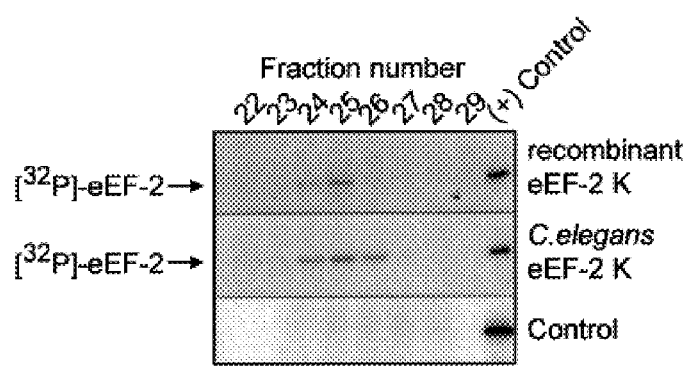
Figure 3C:
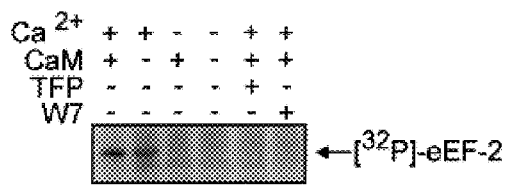
Figure 3D:
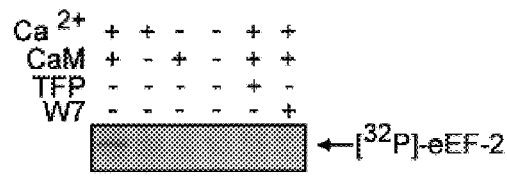

To determine whether Cefk-1 and Cefk-2 have eEF-2 kinase activity, we expressed them in a cell-free coupled transcription/translation system. Translation of Cefk-1 and Cefk-2 produced products with an apparent molecular weight of 100 kDa (FIG. 2), which is slightly larger than the computer-predicted molecular weight of the protein but is identical to the molecular weight of a rabbit reticulocyte eEF-2 kinase as determined by SDS/PAGE. The translation products of the mixture of Cefk-1 and Cefk-2 are able to phosphorylate eEF-2 (FIG. 3) and elute from a Mono Q column at the same position as endogenous *C. elegans* eEF-2 kinase (FIG. 3A). The eEF-2 phosphorylation activity of the recombinant protein is Ca$^{2+}$/calmodulin-dependant (FIG. 3C). We are currently studying whether there are differences in the catalytic properties Cefk-1 and Cefk-2 isoforms.

Mouse and human eEF-2 kinase cDNAs were expressed in a coupled transcription/translation system and a product of ~100 kDa was obtained (FIG. 2). As shown in FIG. 3, the recombinant human eEF-2 kinase activity was strictly Ca$^{2+}$/calmodulin-dependant. The kinase activity was completely inhibited by the calmodulin antagonists trifluoperazine and N-(6-aminohexyl)-5-chloro-1-napthalene-sulfonamide. We have recently expressed human eEF-2 kinase in bacteria as a glutathione S-transferase fusion protein and demonstrated that the ability of the recombinant enzyme to phosphorylate eEF-2 and to undergo autophosphorylation are strictly calmodulin-dependent (data not shown).

EXAMPLE 4

Analysis of Mouse eEF-2 Kinase mRNA Expression in Various Tissues eEF-2 kinase and eEF-2 hybridizations were performed using a 1.6 kb EcoRI mouse cDNA fragment and a 2.6 kb EcoRI human cDNA fragment, respectively. cDNAs were labeled with [$^{32}$P]dCTP using the random-primed DNA labeling method (Feinberg and Vogelstein (1983) *Anal. Biochem.* 132:6–13). A multiple tissue Northern blot (CLONETECH) was prehybridized at 42° C. for 16 h in a 50% formamide solution containing 10×Denhardt's, 5×SSPE, 2% SDS, and 100 μg/ml salmon sperm DNA. Hybridizations were completed in the same solution containing the $^{32}$P-labeled probe (1×10$^6$ cpm/ml; specific activity, ~1×10$^8$ dpm/μg DNA) and 10% dextran sulfate at 42° C. for 16 h. Blots were washed twice at room temperature (15 min) in 2×SSPE, 0.05% SDS, and once at 50° C. (15 min) in 0.5×SSPE, 0.5% SDS. RNA/cDNA hybrids were visualized by autoradiography.

Figure 4:
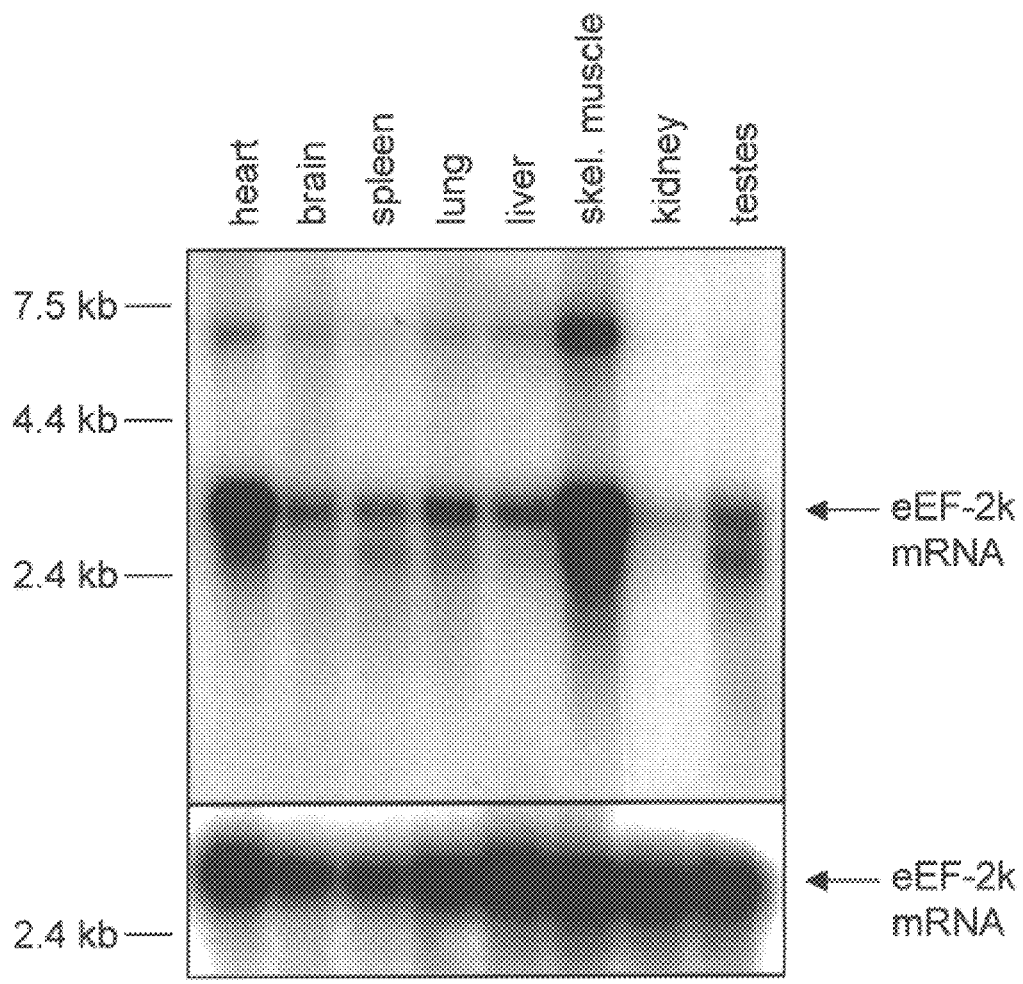
FIG. 4. Northern blot analysis of tissue distribution of mouse eEF-2 kinase mRNA. Northern blots of mouse tissue containing 2 µg of polyadenylated RNA per lane were probed with the random-primed $^{32}$P-labeled mouse eEF-2 kinase cDNA (31). The major transcript appeared at 3.1 kb and minor transcripts at 6.1 and 2.5 kb were also apparent (exposure time, 5 days). The same blots were stripped and rehybridized with a human eEF-2 cDNA (exposure time, 4 days).

Northern blot analysis shows that eEF-2 kinase is ubiquitously expressed in mouse tissues and is particularly abundant in skeletal muscle and heart (FIG. 4). The abundance of eEF-2 kinase mRNA in muscle tissues may indicate that phosphorylation of eEF-2 is particularly important in muscle, or that there are additional substrates of eEF-2 kinase which are muscle-specific.

EXAMPLE 5

Lack of Homology of eEF-2 Kinase to Members of Eukaryotic Protein Kinase Superfamily The alignment of the amino acid sequences of *C. elegans* and mammalian eEF-2 kinases is shown in FIG. 5. Rat and mouse eEF-2 kinase are very similar being 97% identical and differing by only 23 amino acids. Human eEF-2 kinase is 90% identical to mouse and rat eEF-2 kinase. In contrast, *C. elegans* eEF-2 kinase is found to be only 40% identical to mammalian eEF-2 kinase.

According to the current classification, eEF-2 kinase belongs to the family of closely related calmodulin-dependent protein kinases. Surprisingly, upon analyzing eEF-2 kinase sequences, we did not find any homology to the other calmodulin-dependent kinases or to any other members of the protein kinase super-family. The only motif which it shares with all other protein kinases is the GXGXXG motif (279–284 in *C. elegans* eEF-2 kinases; 295–300 in mouse eEF-2 kinase) which forms a glycine-rich loop and is part of the ATP-binding site. Comparison of mammalian and *C. elegans* eEF-2 kinase revealed only one extended region of homology that spans ~200 amino acids upstream of the GXGXXG motif. The high degree of similarity and the proximity to the nucleotide-binding site suggests that these 200 amino acids represent the catalytic domain. This region has a high degree of similarity and a portion of this region (amino acids 251–300 in mouse eEF-2 kinase) displays 75% identity to the catalytic domain of MHCKA (see below), which also suggests that this is the catalytic domain. In the recently published rat eEF-2 kinase sequence [Redpath et al., *J. Biol. Chem.* 271: 17547–17554 (1996)], the catalytic domain was predicted to reside between amino acids 288 and 554 based on the homology with the catalytic domain of cAMP-dependant protein kinase (PKA). Our results demonstrate that their prediction cannot be correct for several reasons. First, we find that the homology of this region with PKA is not statistically significant. Second, this region is the least conserved between mammalian and *C. elegans* eEF-2 kinase. Finally, according to secondary structure predictions [made by Alexei V. Finkelstein, Institute of Protein Research, Russia using the ALB-GLOBULE program [Ptitsyn and Finkelstein, *Biopolymers* 22:15–25 (1983)]], this region most likely has a distorted structure and contains almost no α-helices or β-strands, which are characteristic of a catalytic domain.

Because eEF-2 kinase is $CA^{2+}$/calmodulin-dependant, it should contain a calmodulin-binding domain, which is usually represented by an amphipathic α-helix. There are several regions that could possibly assume an amphipathic α-helical conformation. Further biochemical analysis is required to determine which of these is the calmodulin-binding domain.

In the C-terminal region, there is a short stretch of 22 amino acids which is 86% identical between mammalian and *C. elegans* eEF-2 kinase and is preceded by a longer region of weak homology. We do not know the function of this conserved region at present. One of the possibilities is that it is that it is involved in oligomerization of the kinase. It was thought previously that eEF-2 kinase was an elongated monomer because it migrated during gel filtration as an ~150-kDa protein and migrated on SDS gels as a 105-kDa polypeptide [Ryazanov and Spirin, *Translational Regulation of Gene Expression*, Pienum, NY, Vol 2, pp 433–455 (1993); Abdelnajid et al., *Int. J. Dev. Biol.*, 37:279–290 (1993)]. However, the molecular weight of a monomer of mammalian eEF-2 kinase based on the predicted sequence is just 82 kDa. Thus, it is possible that eEF-2 kinase is not a monomer but a responsible for dimerization. Interestingly, according to computer prediction using the COIL program, this conserved region can form a coiled-coil. Formation of coiled-coil is often responsible for dimerization [Lupas, *Trends Biochem. Sci.*, 21:375–382 (1996)].

EXAMPLE 6

Striking Homology Between eEF-2 Kinase and MHCK A from Dictyostelium

We found that eEF-2 kinases is homologous to the central portion of the recently described MHCKA from Dictyostelium [Futey et al., *J. Biol. Chem.* 270:523–529 (1995) see FIG. 5]. The kinase was biochemically identified as a 130-kDa protein and has a demonstrated role in myosin assembly, both in vitro and in vivo [Futey et al., 1995, supra]. As with eEF-2 kinase, MHCKA displays no region with detectable similarity to the conserved catalytic domains found in known eukaryotic protein kinases. Primary structure analysis of MHCKA revealed an amino-terminal domain with a probable coiled-coil structure, a central nonrepetitive domain, and a C-terminal domain consisting of seven WD repeats [Futey et al., 1995, supra]. A fragment of the central nonrepetitive domain of MHCKA containing amino acids 552–841 was recently shown to represent the catalytic domain [Cote et al., *J. Biol. Chem.* 272:6846–6849 (1997)].

Figure 6:
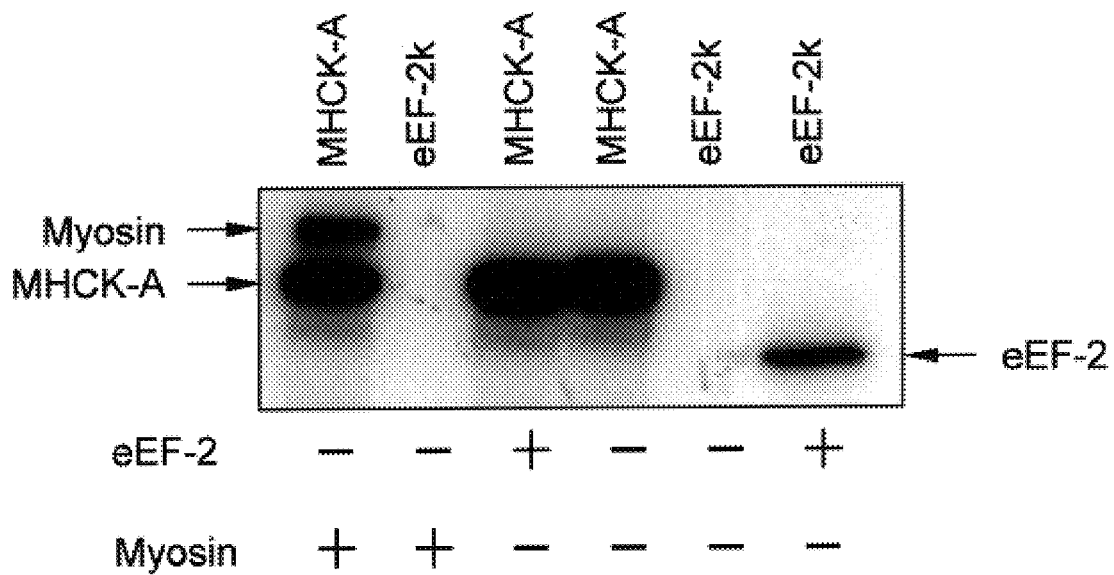
FIG. 6. Substrate specificity of eEF-2 kinase and MHCK A. Phosphorylation assays containing eEF-2 kinase (~50 ng) or MHCK A (0.2 µg) and either 0.5 µg rabbit reticulocyte eEF-2 or 0.1 µg Dictyostelium myosin were performed under standard conditions except that incubation time was extended to 10 min.

Because the catalytic domain of MHCKA and eEF-2 kinase have a high degree of similarity, the substrate specificity of these two kinases was assayed. FIG. 6 shows that MHCK A cannot phosphorylate eEF-2, and likewise, rabbit eEF-2 kinase cannot use myosin heavy chains as a substrate. This demonstrated that each of these kinases is specific for their respective substrates.

EXAMPLE 7 eEF-2 Kinase and MHCK A Define a New Class of Protein Kinases

Figure 7:
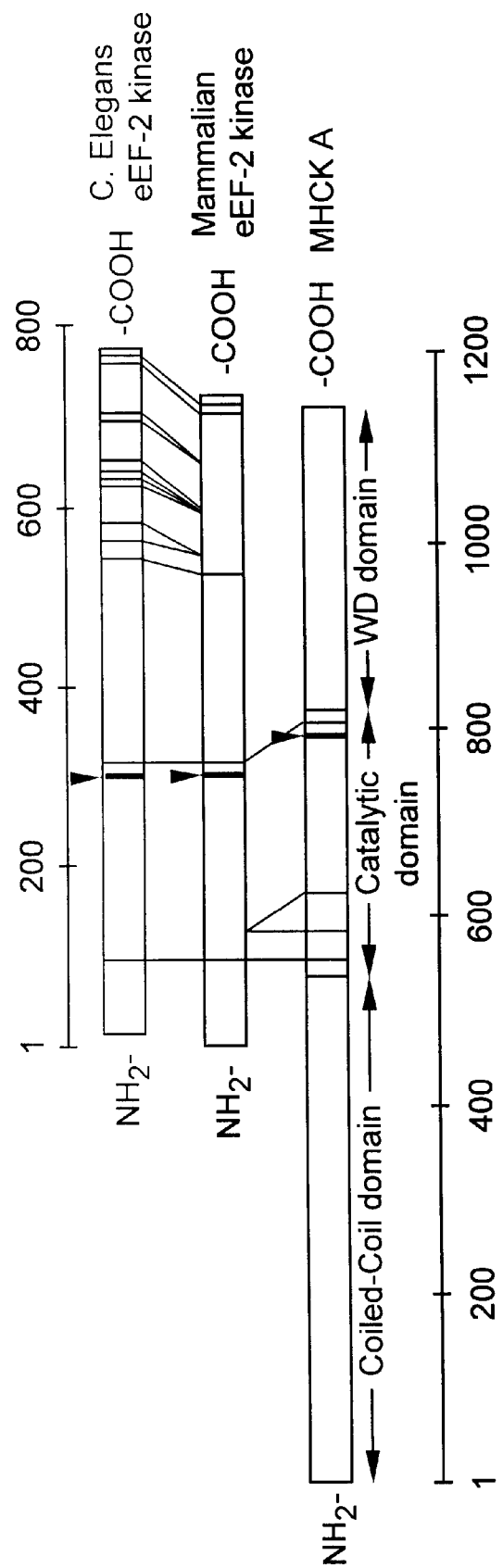
FIG. 7. Schematic representation of the structure of mammalian and *C. elegans* eEF-2 kinases and MHCK A. The homologous regions are represented by dark shading. The regions of weak similarity are represented by light shading. The position of the GXGXXG motif is indicated by vertical arrows.

Members of the eukaryotic protein kinase superfamily are characterized by a conserved catalytic domain containing approximately 260 amino acids and is divided into twelve subdomains [Hanks and Hunter, *FASEB J.*, 9:576–596 (1996); Hardie and Hanks, *The Protein Kinase Facts Book*, Academic, London (1995), Taylor et al., *Annu. Rev. Cell Biol.* 8:429–462 (1992) Johnson et al., *Cell.* 85: 149–158 (1996)]. The three-dimensional structure of several protein kinases revealed that the catalytic domain consists of two lobes. The smaller N-terminal lobe, which has a twisted β-sheet structure, represents the ATP-binding domain. The larger C-terminal lobe, which is predominantly α-helical is involved in substrate binding. At the primary structure level, the only motif similar between eEF-2 kinase, MHCK A, and other protein kinases is the GXGXXG motif which forms the loop interacting directly with the phosphates of ATP [Hanks and Hunter, 1996, supra; Hardie and Hanks 1995, supra; Taylor et al., supra]. In eukaryotic protein kinases, this motif is located at the very N terminus of the ATP-binding lobe of the catalytic domain. In contrast, in a eEF-2 kinase and MHCK A, this motif is close to the C terminus of the catalytic domain (see FIG. 7). However, the overall topology of the ATP-binding subdomain of eEF-2 kinase and MHCK A can be similar to other protein kinases because the region upstream of the GXGXXG motif is strongly predicted to contain four or five β-strands and thus can form a twisted β-sheet.

However, the mechanism of ATP-binding to eEF-2 kinase is probably quite different in comparison to other conventional members of the eukaryotic protein kinase superfamily. In protein kinases, there is a conserved lysine residue, corresponding to Lys-72 in cAMP-dependant protein kinases which binds to the β- and γ-phosphates of ATP and is located at about 20 amino acids downstream of the GXGXXG motif. Analysis of eEF-2 kinase and MHCK A sequences revealed that there are no conserved lysine residues in the vicinity of the GXGXXG motif. There is another atypical protein kinase, BCR-ABLE, which does not contain this conserved lysine and it is proposed that it interacts with ATP via two cysteine residues [Maro and Witte, Cell, 67:459–468 (1991)]. Interestingly, eEF-2 kinase and MHCK-A contain two conserved cysteine residues (Cys-313 and Cys-317 in mouse eEF-2 kinase) which are located near the GXGXXG motif and therefore might be involved in ATP binding. Thus the mechanism of ATP-binding of eEF-2 kinase and MHCK A is different from other members of the protein kinase superfamily, but may be similar to that of the BCR-ABLE protein kinase.

The overall catalytic mechanism of eEF-2 kinase and MHCKA is probably also very different from other eukaryotic protein kinases. All members of the eukaryotic protein kinase superfamily contain a DXXXN motif in the catalytic loop and a DFG motif in the activation segment [Hanks and Hunter, 1996; supra, Hardie and Hanks 1995, supra; Taylor et al., supra; Johnson et al., 1996, supra]. These two motifs, which are directly involved in the catalysis of the protein phosphorylation reaction, are absent from the eEF-2 kinase and MHCK A catalytic domain.

We do not know at the present time whether there are other protein kinases which are structurally similar to eEF-2 kinase and MHCK A. An extensive search of the entire nonrestricted database of the National Center for Biotechnology Information using the BLAST program did not reveal any protein with a significant homology to the catalytic domain of eEF-2 kinase and MHCKA. A search of the Expressed Sequence Tag (EST) database revealed several ESTs from C. elegans, mouse and human which are essentially identical to portions of eEF-2 kinase cDNA sequences reported here. Interestingly, a search of the recently completed genome database of Saccharomyces cerevisiae did not reveal any protein with homology to eEF-2 kinase despite the fact that eEF-2 phosphorylation was reported in yeast (41).

Conclusion

Since the catalytic domains of eEF-2 kinase and MHCK A do not share homology with other known protein kinases, these two protein kinases establish the presence of a novel and widespread superfamily of eukaryotic protein kinases. Although the existence of several unusual protein kinases have been reported, to our knowledge, we demonstrate for the first time the existence of a biochemically well-characterized and ubiquitous protein kinase that is structurally unrelated to other serine/threonine/tyrosine kinases. Contrary to the widely accepted belief that all eukaryotic protein kinases evolved from a single ancestor, our results suggest that eukaryotic protein kinases appeared at least twice during the course of evolution. This also suggests that, in addition to the relatively well-characterized catalytic mechanism employed by members of eukaryotic serine/threonine/tyrosine protein kinase superfamily, there exists another mechanism of protein kinase superfamily, there exists another mechanism of protein phosphorylation. Further studies will reveal the molecular details of this mechanism and whether there are other protein kinases that phosphorylate their substrates using this mechanism.

EXAMPLE 8

Preparation of Recombinant eEF-2 kinase Fusion Proteins with GST, 6xHis, and Thioredoxin Human eEF-2 kinase cDNA was cloned into three different expression vectors: pGEX-2T (Pharmacia Biotech, Piscataway, N.J.); pRSET A (Invitrogen, Sorrento Valley, Calif.); and, pThioHisB (Invitrogen). After transformation into Escherichia coli strain BL21(DE3), transformants were cultured in LB broth containing 50 μg/ml ampicillin. When the cultured reached an $A_{600}$ value of 0.7, isopropyl-β-thiogalactopyranoside (IPTG) was added to the bacterial cultures to a final concentration of 0.5 μM to induce expression. After three hours, the cultures were harvested by centrifugation, and the cells were then sonicated. After extract preparation and analysis by SDS-PAGE, it was found that all of the expressed tag forms of the eEF-2 kinase were in inclusion bodies. Inclusion bodies were precipitated, dissolved in 8.0 M urea, and dialyzed overnight against 20 mM Tris-HCl (ph. 7.0) buffer containing 100 mM NaCl and 4 mM β-mercaptoethanol. The refolded protein was analyzed by SDS-PAGE and assayed for the ability to phosphorylate eEF-2. All of the fusion eEF-2 kinase preparations were able to efficiently phosphorylate eEF-2 (data not shown).

EXAMPLE 9 eEF-2 Kinase Activity Assay Using a 16-Amino Acid Peptide Derived from Myosin Heavy Chain as the Phosphorylation Target We found that 16' mer peptide, RKKFGESEKTKTKEFL, (SEQ ID NO:20) can serve as a good substrate for eEF-2 kinase. (Note: circular dichroism measurements (data not shown) indicated that this peptide is in an α-helical structure, and that amidation of the peptide further stabilizes the α-helical structure, resulting in stronger phosphoacceptor activity.) Since recombinant eEF-2 is impossible to overexpress, as discussed supra, and large amounts of the protein are required to for large scale screening assays, the discovery of a peptide (easily synthesized on a large scale) that exhibits the same phosphoacceptor activity as eEF-2 was the critical breakthrough that allows for the development of a variety of automated high throughput screening assays for screening drug candidates.

Figure 8:
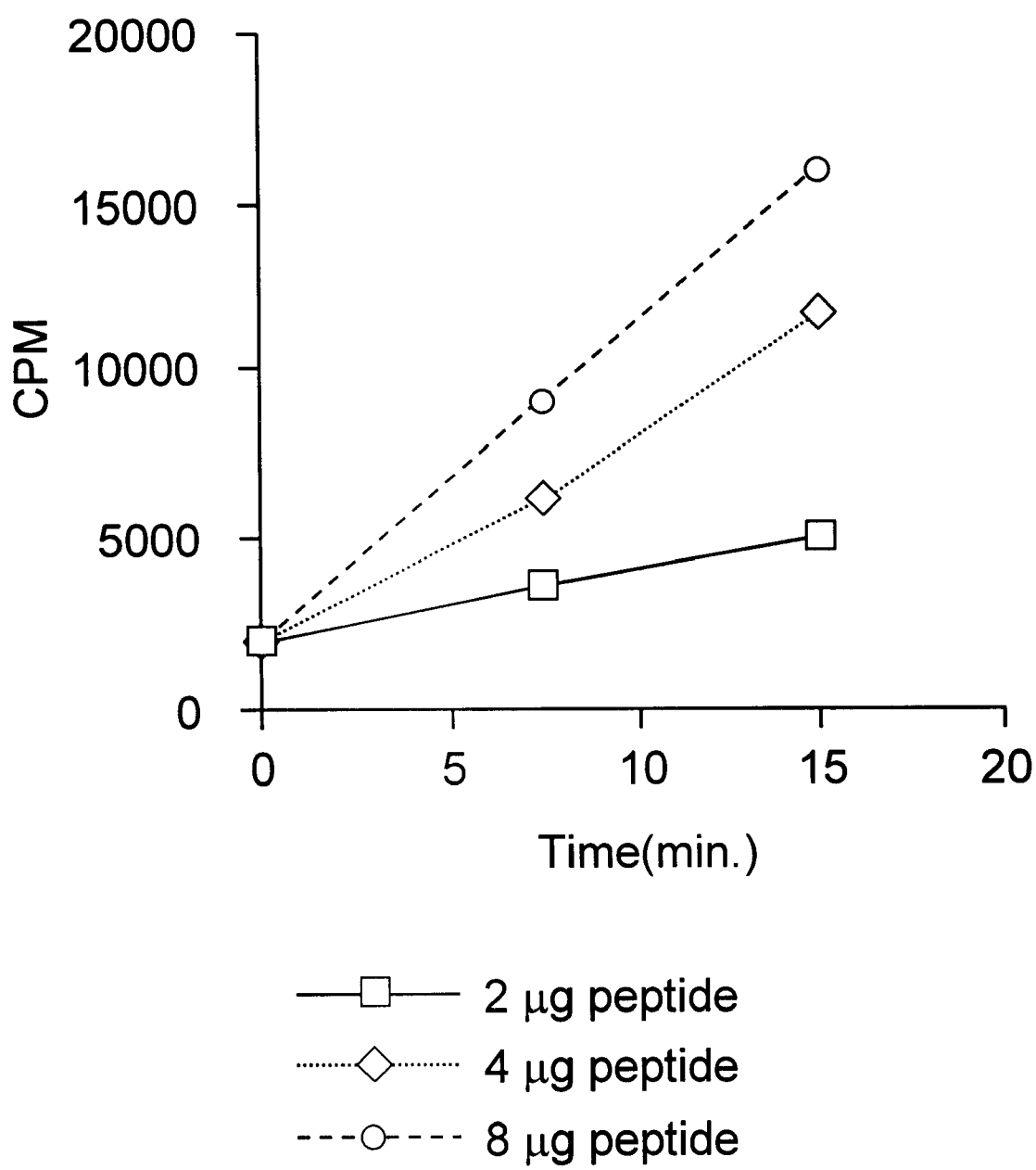
FIG. 8. Assay for eEF-2 kinase activity. Recombinant eEF-2 kinase (2 µg) was incubated with increasing concentrations of a peptide phosphorylation target (RKKGESEKTKTKEFL) in a buffer consisting of 12.5 mM Hepes-KOH (pH 7.4), 2.5 mM magnesium acetate, 1.25 mM DTT, 25 µM $CaCl_2$, 0.5 µg calmodulin, 100 µM ATP, and 0.5 µCi [γ-$^{33}$P]ATP in a total volume of 50 µl. Samples were incubated at 30° C. and aliquots were withdrawn at various time points, and the reaction was terminated by incubation in an ice water bath. The aliquots were then spotted onto phosphocellulose paper (2 cm×2 cm) and washed (4×4 min) with 75 mM phosphoric acid. The papers were then rinsed with 100% ethanol, dried, and then counted in a scintillation counter.

The basic assay is as follows: 0.2–10.0 yg of recombinant eEF-2 kinase (produced as described in EXAMPLE 6) is incubated with the 16' mer peptide (described above) in a buffer consisting of 12.5 mM Hepes-KOH (ph. 7.4), 2.5 mM magnesium acetate, 1.25 mM DTT, 25 μM $CaCl_2$, 0.05–2.5 μg calmodulin, 100 μM ATP, and 0.5 μCi [γ-$^{33}$P]ATP in a total volume of 5–250 μl. Samples are incubated at 30° C. and aliquots can be withdrawn at various time points or at a single end point, and the reaction terminated by lowering the temperature ($\leq$4° C.). The aliquots are then spotted onto phosphocellulose paper (2 cm×2 cm) and washed (4×4 min) with 75 mM phosphoric acid. The papers are then rinsed with 100% ethanol, dried, and then counted in a scintillation counter. The assay can be performed at various peptide concentrations, as we did in the experiment illustrated in FIG. 8. Clearly for a high throughput drug screening assay, that would be amenable to automation, the assays would most likely be performed using one peptide concentration with increasing amounts of different drug (inhibitor) candidates, and the data collected at a single time point. The assay can be performed in any one of the following formats:

1. with [γ-$^{32}$P]ATP or [γ-$^{33}$P]ATP and then detected using either standard scintillation counting, or detected in the format of a homogeneous assay using a Scintillation Proximity Assay, described in detail in both the Amersham Product Catalog (1997), pp. 252–258, and U.S. Pat. No. 4,568,649;

2. in any of a number of standard immunoassay formats using antibodies that are specific for the phosphorylated form of the 16' mer peptide. Detection would then be, as described in more detail supra, through the use of either isotopically- or nonisotopically-labeled antibodies, secondary antibodies, or 16' mer peptide.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. An isolated eukaryotic elongation factor-2 kinase (eEF-2 kinase) capable of phosphorylating an amino acid within an alpha helical domain of eukaryotic elongation factor-2 (eEF-2), said kinase comprising an amino acid sequence selected from the group consisting of SEQ ID NO:2, SEQ ID NO:4 and SEQ ID NO:10.

2. The eEF-2 kinase of claim 1 which is derived from mammalian cells.

3. The eEF-2 kinase of claim 1 which is derived from human cells.

4. The eEF-2 kinase of claim 1 which is derived from mouse cells.

5. The eEF-2 kinase of claim 1 labeled with a detectable label.

6. The eEF-2 kinase of claim 5 wherein the label is selected from enzymes, chemicals which fluoresce and radioactive elements.

7. An isolated human eEF-2 kinase capable of phosphorylating an amino acid within an alpha helical domain of eukaryotic elongation factor-2 (eEF-2), said kinase comprising the amino acid sequence of SEQ ID NO:2.

8. A method for detecting the eEF-2 kinase of claim 1 and assessing eEF-2 kinase levels by:

A. contacting a biological sample from a mammal in which the presence or activity of said eEF-2 kinase is suspected with a binding partner selected from the group of human eEF-2, mouse eEF-2, a peptide fragment thereof, or a peptide fragment of eukaryotic myosin heavy chain (MHC), under conditions that allow binding of said eEF-2 kinase to said binding partner to occur; and B. detecting whether binding has occurred, and to what degree; wherein the detection of binding indicates the presence or activity of said eEF-2 kinase in said sample, and indicates a level of said eEF-2 kinase in said sample.

9. The method of claim 8 wherein said peptide fragment of MHC has the sequence set out in SEQ ID NO: 20.

10. An assay system for screening drugs and other agents for the ability to modulate human or mouse eukaryotic elongation factor-2 kinase (eEF-2 kinase) activity, comprising combining a predetermined amount of the eEF-2 kinase of claim 1 with varying amounts of said drug or other agent, along with a target protein which the kinase can phosphorylate and ATP; wherein detection is via either a detectable label on the γ-phosphate of ATP or an antibody directed against a target protein which the kinase can phosphorylate.

11. The assay system of claim 10 wherein the target protein is selected from the group of human eEF-2, mouse eEF-2, a peptide fragment thereof, or a peptide fragment of eukaryotic myosin heavy chain (MHC).

12. The assay system of claim 11 wherein said peptide fragment of MHC has the sequence set out in SEQ ID NO:20.

13. An assay system for screening drugs and other agents for the ability to modulate human or mouse eukaryotic elongation factor-2 kinase (eEF-2 kinase) activity, comprising combining a predetermined amount of the eEF-2 kinase of claim 1 or 7 with varying amounts of said drug or other agent, along with a target protein selected from the group of human eEF-2, mouse eEF-2, a peptide fragment thereof, or a peptide fragment of eukaryotic myosin heavy chain (MHC), and ATP; wherein detection is via either a detectable label on the γ-phosphate of ATP or an antibody directed against said target porotein.

14. The assay system of claim 10 or 13 wherein the label on the γ-phosphate of ATP comprises one of the following:

A. $^{32}P$;

B. $^{33}P$

C. $^{35}S$

D. a biotinylated phosphate moiety; or,

E. a fluorescent phosphate moiety.

15. The assay system of claim 10 or 13 wherein the label on the antibody comprises one of the following:

A. an enzyme detectable with calorimetric, fluorescent, or chemiluminescent substrates, such as alkaline phosphatase or horseradish peroxidase;

B. a biotin moiety;

C. a fluorescent moiety; or,

D. a radioactive moiety chosen from the following group of isotopes: $^{3}H$, $^{14}C$, $^{32}P$, $^{33}P$, $^{35}S$, $^{36}Cl$, $^{51}Cr$, $^{57}Co$, $^{58}Co$, $^{59}Fe$, $^{90}Fe$, $^{90}Y$, $^{125}I$, $^{131}I$, and $^{186}Re$.

16. An assay system for screening drugs and other agents for ability to modulate the activity of the eEF-2 kinase of claim 1, comprising:

A. culturing an observable cellular test colony inoculated with a drug or agent;

B. harvesting a supernatant from said cellular test colony; and,

C. examining said supernatant for the presence of said eEF-2 kinase activity wherein an increase or a decrease in a level of said eEF-2 kinase activity indicates the ability of a drug to modulate the activity of said eEF-2 kinase.

17. A test kit for assessing the level of activity of the eEF-2 kinase of claim 1 in a eukaryotic cellular sample, comprising:

A. a predetermined amount of a detectably labeled specific binding partner of eEF-2 kinase selected from the group of human eEF-2, mouse eEF-2, a peptide fragment thereof, or a peptide fragment of eukaryotic myosin heavy chain (MHC);

B. other reagents; and,

C. directions for use of said kit.

* * * * *

UNITED STATES PATENT AND TRADEMARK OFFICE
CERTIFICATE OF CORRECTION

PATENT NO.     : 6,346,406 B1
DATED          : February 12, 2002
INVENTOR(S)    : Ryazanov et al.

It is certified that error appears in the above-identified patent and that said Letters Patent is hereby corrected as shown below:

Column 1,
Line 4, add the following:

-- GOVERNMENT RIGHTS

The research leading to the present invention was supported, in part, by the following grants from the National Institute of Health: GM57300 and CA08112. Accordingly, the United States Government may have certain rights in the invention. --

Signed and Sealed this

First Day of October, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
        (A) LENGTH: 2178 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:1:

```
ATGGCAGACG AAGACCTCAT CTTCCGCCTG GAAGGTGTTG ATGGCGGCCA GTCCCCCCGA      60

GCTGGCCATG ATGGTGATTC TGATGGGGAC AGCGACGATG AGGAAGGTTA CTTCATCTGC     120

CCCATCACGG ATGACCCAAG CTCGAACCAG AATGTCAATT CCAAGGTTAA TAAGTACTAC     180

AGCAACCTAA CAAAAAGTGA GCGGTATAGC TCCAGCGGGT CCCCGGCAAA CTCCTTCCAC     240

TTCAAGGAAG CCTGGAAGCA CGCAATCCAG AAGGCCAAGC ACATGCCCGA CCCCTGGGCT     300

GAGTTCCACC TGGAAGATAT TGCCACCGAA CGTGCTACTC GACACAGGTA CAACGCCGTC     360

ACCGGGGAAT GGCTGGATGA TGAAGTTCTG ATCAAGATGG CATCTCAGCC CTTCGGCCGA     420

GGAGCAATGA GGGAGTGCTT CCGGACGAAG AAGCTCTCCA ACTTCTTGCA TGCCCAGCAG     480

TGGAAGGGCC CCTCCAACTA CGTGGCGAAG CGCTACATCG AGCCCGTAGA CCGGGATGTG     540

TACTTTGAGG ACGTGCGTCT ACAGATGGAG GCCAAGCTCT GGGGGGAGGA GTATAATCGG     600

CACAAGCCCC CCAAGCAGGT GGACATCATG CAGATGTGCA TCATCGAGCT GAAGGACAGA     660

CCGGGCAAGC CCCTCTTCCA CCTGGAGCAC TACATCGAGG GCAAGTACAT CAAGTACAAC     720

TCCAACTCTG GCTTTGTCCG TGATGACAAC ATCCGACTGA CGCCGCAGGC CTTCAGCCAC     780

TTCACTTTTG AGCGTTCCGG CCATCAGCTG ATAGTGGTGG ACATCCAGGG AGTTGGGGAT     840

CTCTACACTG ACCCACAGAT CCACACGGAG ACGGGCACTG ACTTTGGAGA CGGCAACCTA     900

GGTGTCCGCG GGATGGCGCT CTTCTTCTAC TCTCATGCCT GCAACCGGAT TTGCGAGAGC     960

ATGGGCCTTG CTCCCTTTGA CCTCTCGCCC GGGAGAGGG ATGCAGTGAA TCAGAACACC    1020

AAGCTGCTGC AATCAGCCAA GACCATCTTG AGAGGAACAG AGGAAAAATG TGGGAGCCCC    1080

CGAGTAAGGA CCCTCTCTGG GAGCCGGCCA CCCCTGCTCC GTCCCCTTTC AGAGAACTCT    1140
```

-continued

```
GGAGACGAGA ACATGAGCGA CGTGACCTTC GACTCTCTCC CTTCTTCCCC ATCTTCGGCC    1200

ACACCACACA GCCAGAAGCT AGACCACCTC CATTGGCCAG TGTTCAGTGA CCTCGATAAC    1260

ATGGCATCCA GAGACCATGA TCATCTAGAC AACCACCGGG AGTCTGAGAA TAGTGGGGAC    1320

AGCGGATACC CCAGTGAGAA GCGGGGTGAG CTGGATGACC CTGAGCCCCG AGAACATGGC    1380

CACTCATACA GTAATCGGAA GTACGAGTCT GACGAAGACA GCCTGGGCAG CTCTGGACGG    1440

GTATGTGTAG AGAAGTGGAA TCTCCTCAAC TCCTCCCGCC TCCACCTGCC GAGGGCTTCG    1500

GCCGTGGCCC TGGAAGTGCA AAGGCTTAAT GCTCTGGACC TCGAAAAGAA AATCGGGAAG    1560

TCCATTTTGG GGAAGGTCCA TCTGGCCATG GTGCGCTACC ACGAGGGTGG GCGCTTCTGC    1620

GAGAAGGGCG AGGAGTGGGA CCAGGAGTCG GCTGTCTTCC ACCTGGAGCA CGCAGCCAAC    1680

CTGGGCGAGC TGGAGGCCAT CGTGGGCCTG GGACTCATGT ACTCGCAGTT GCCTCATCAC    1740

ATCCTAGCCG ATGTCTCTCT GAAGGAGACA AAGAGAACA AAACCAAAGG ATTTGATTAC    1800

TTACTAAAGG CCGCTGAAGC TGGCGACAGG CAGTCCATGA TCCTAGTGGC GCGAGCTTTT    1860

GACTCTGGCC AGAACCTCAG CCCGGACAGG TGCCAAGACT GGCTAGAGGC CCTGCACTGG    1920

TACAACACTG CCCTGGAGAT GACGGACTGT GATGAGGGCG GTGAGTACGA CGGAATGCAG    1980

GACGAGCCCC GGTACATGAT GCTGGCCAGG GAGGCAGAGA TGCTGTTCAC AGGAGGCTAC    2040

GGGCTGGAGA AGGACCCGCA GAGATCAGGG GACTTGTATA CCCAGGCAGC AGAGGCAGCG    2100

ATGGAAGCCA TGAAGGGCCG ACTGGCCAAC CAGTACTACC AAAAGGCTGA AGAGGCCTGG    2160

GCCCAGATGG AGGAATAA                                                  2178
```

(2) INFORMATION FOR SEQ ID NO:2:

(i) SEQUENCE CHARACTERISTICS:
        (A) LENGTH: 725 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO:2:

```
Met Ala Asp Glu Asp Leu Ile Phe Arg Leu Glu Gly Val Asp Gly Gly
1               5                   10                  15

Gln Ser Pro Arg Ala Gly His Asp Gly Asp Ser Asp Gly Asp Ser Asp
            20                  25                  30

Asp Glu Glu Gly Tyr Phe Ile Cys Pro Ile Thr Asp Asp Pro Ser Ser
        35                  40                  45

Asn Gln Asn Val Asn Ser Lys Val Asn Lys Tyr Tyr Ser Asn Leu Thr
    50                  55                  60

Lys Ser Glu Arg Tyr Ser Ser Ser Gly Ser Pro Ala Asn Ser Phe His
65                  70                  75                  80

Phe Lys Glu Ala Trp Lys His Ala Ile Gln Lys Ala Lys His Met Pro
                85                  90                  95

Asp Pro Trp Ala Glu Phe His Leu Glu Asp Ile Ala Thr Glu Arg Ala
            100                 105                 110

Thr Arg His Arg Tyr Asn Ala Val Thr Gly Glu Trp Leu Asp Asp Glu
        115                 120                 125
```

-continued

```
Val Leu Ile Lys Met Ala Ser Gln Pro Phe Gly Arg Gly Ala Met Arg
    130                 135                 140
Glu Cys Phe Arg Thr Lys Lys Leu Ser Asn Phe Leu His Ala Gln Gln
145                 150                 155                 160
Trp Lys Gly Ala Ser Asn Tyr Val Ala Lys Arg Tyr Ile Glu Pro Val
                165                 170                 175
Asp Arg Asp Val Tyr Phe Glu Asp Val Arg Leu Gln Met Glu Ala Lys
            180                 185                 190
Leu Trp Gly Glu Glu Tyr Asn Arg His Lys Pro Pro Lys Gln Val Asp
        195                 200                 205
Ile Met Gln Met Cys Ile Ile Glu Leu Lys Asp Arg Pro Gly Lys Pro
    210                 215                 220
Leu Phe His Leu Glu His Tyr Ile Glu Gly Lys Tyr Ile Lys Tyr Asn
225                 230                 235                 240
Ser Asn Ser Gly Phe Val Arg Asp Asp Asn Ile Arg Leu Thr Pro Gln
                245                 250                 255
Ala Phe Ser His Phe Thr Phe Glu Arg Ser Gly His Gln Leu Ile Val
            260                 265                 270
Val Asp Ile Gln Gly Val Gly Asp Leu Tyr Thr Asp Pro Gln Ile His
        275                 280                 285
Thr Glu Thr Gly Thr Asp Phe Gly Asp Gly Asn Leu Gly Val Arg Gly
    290                 295                 300
Met Ala Leu Phe Phe Tyr Ser His Ala Cys Asn Arg Ile Cys Glu Ser
305                 310                 315                 320
Met Gly Leu Ala Pro Phe Asp Leu Ser Pro Arg Glu Arg Asp Ala Val
                325                 330                 335
Asn Gln Asn Thr Lys Leu Leu Gln Ser Ala Lys Thr Ile Leu Arg Gly
            340                 345                 350
Thr Glu Glu Lys Cys Gly Ser Pro Arg Val Arg Thr Leu Ser Gly Ser
        355                 360                 365
Arg Pro Pro Leu Leu Arg Pro Leu Ser Glu Asn Ser Gly Asp Glu Asn
    370                 375                 380
Met Ser Asp Val Thr Phe Asp Ser Leu Pro Ser Ser Pro Ser Ser Ala
385                 390                 395                 400
Thr Pro His Ser Gln Lys Leu Asp His Leu His Trp Pro Val Phe Ser
                405                 410                 415
Asp Leu Asp Asn Met Ala Ser Arg Asp His Asp His Leu Asp Asn His
            420                 425                 430
Arg Glu Ser Glu Asn Ser Gly Asp Ser Gly Tyr Pro Ser Glu Lys Arg
        435                 440                 445
Gly Glu Leu Asp Asp Pro Glu Pro Arg Glu His Gly His Ser Tyr Ser
    450                 455                 460
Asn Arg Lys Tyr Glu Ser Asp Glu Asp Ser Leu Gly Ser Ser Gly Arg
465                 470                 475                 480
Val Cys Val Glu Lys Trp Asn Leu Leu Asn Ser Ser Arg Leu His Leu
                485                 490                 495
Pro Arg Ala Ser Ala Val Ala Leu Glu Val Gln Arg Leu Asn Ala Leu
            500                 505                 510
Asp Leu Glu Lys Lys Ile Gly Lys Ser Ile Leu Gly Lys Val His Leu
        515                 520                 525
Ala Met Val Arg Tyr His Glu Gly Gly Arg Phe Cys Glu Lys Gly Glu
    530                 535                 540
```

-continued

```
Glu Trp Asp Gln Glu Ser Ala Val Phe His Leu Glu His Ala Ala Asn
545                 550                 555                 560

Leu Gly Glu Leu Glu Ala Ile Val Gly Leu Gly Leu Met Tyr Ser Gln
                565                 570                 575

Leu Pro His His Ile Leu Ala Asp Val Ser Leu Lys Glu Thr Glu Glu
                580                 585                 590

Asn Lys Thr Lys Gly Phe Asp Tyr Leu Leu Lys Ala Ala Glu Ala Gly
                595                 600                 605

Asp Arg Gln Ser Met Ile Leu Val Ala Arg Ala Phe Asp Ser Gly Gln
                610                 615                 620

Asn Leu Ser Pro Asp Arg Cys Gln Asp Trp Leu Glu Ala Leu His Trp
625                 630                 635                 640

Tyr Asn Thr Ala Leu Glu Met Thr Asp Cys Asp Glu Gly Gly Glu Tyr
                645                 650                 655

Asp Gly Met Gln Asp Glu Pro Arg Tyr Met Met Leu Ala Arg Glu Ala
                660                 665                 670

Glu Met Leu Phe Thr Gly Gly Tyr Gly Leu Glu Lys Asp Pro Gln Arg
                675                 680                 685

Ser Gly Asp Leu Tyr Thr Gln Ala Ala Glu Ala Ala Met Glu Ala Met
690                 695                 700

Lys Gly Arg Leu Ala Asn Gln Tyr Tyr Gln Lys Ala Glu Glu Ala Trp
705                 710                 715                 720

Ala Gln Met Glu Glu
                725
```

(2) INFORMATION FOR SEQ ID NO:3:

(i) SEQUENCE CHARACTERISTICS:
        (A) LENGTH: 2175 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Mus musculus (xi) SEQUENCE DESCRIPTION: SEQ ID NO:3:

```
ATGGCAGACG AAGACCTCAT CTTCTGCCTG GAAGGTGTTG ACGGTGGCAG GTGCTCCCGA      60

GCTGGCCACA ATGCGGACTC TGACACAGAC AGTGACGATG ATGAGGGCTA TTTCATCTGC     120

CCCATCACTG ATGACCACAT GTCCAATCAG AATGTCAGCT CCAAAGTCCA GAGCTACTAT     180

AGCAACCTAA CAAAAACAGA GTGCGGCTCC ACAGGGTCAC CAGCCAGCTC CTTCCACTTC     240

AAGGAAGCCT GGAAGCATGC GATCGAGAAA GCCAAGCACA TGCCTGACCC CTGGGCTGAA     300

TTCCATCTCG AGGACATCGC CACAGAACAT GCTACTCGGC ACAGGTACAA CGCTGTCACC     360

GGGGAATGGC TGAAAGACGA GGTTCTGATC AAGATGGCGT CTCAGCCCTT CGGCCGTGGA     420

GCAATGAGGG AGTGCTTCAG GACGAAGAAA CTCTCCAACT TCTTGCACGC CAGCAATGG      480

AAGGGGGCCT CCAACTACGT GGCCAAGCGC TACATCGAGC CGGTGGACAG GAGCGTGTAC     540

TTTGAGGATG TGCAGCTCCA GATGGAGGCG AAGCTCTGGG GGGAGGATTA CAATCGGCAC     600

AAGCCCCCCA AGCAGGTGGA TATCATGCAG ATGTGCATCA TTGAGCTAAA GGACAGACCA     660

GGCCAGCCCC TCTTCCACTT GGAGCACTAC ATTGAGGGCA AGTACATCAA GTACAATTCC     720
```

-continued

```
AACTCAGGCT TTGTCCGTGA TGACAACATC CGACTAACCC CACAGGCCTT CAGCCATTTC      780

ACATTTGAGC GTTCTGGTCA TCAGCTGATT GTAGTGGACA TCCAGGGTGT GGGTGACCTT      840

TATACCGACC CACAGATCCA CACTGAGAAA GGCACTGACT TTGGAGATGG TAACCTTGGT      900

GTCCGGGGAA TGGCTCTCTT CTTCTACTCT CATGCCTGCA ACCGGATTTG TCAGAGCATG      960

GGCCTTACGC CCTTTGACCT CTCCCCACGG GAACAGGATG CGGTGAATCA GAGCACCAGG     1020

CTATTGCAAT CAGCCAAGAC CATCTTGAGG GGGACAGAGG AGAAGTGTGG GAGTCCCCGC     1080

ATAAGGACAC TCTCTAGCAG CCGGCCCCCT TTGCTCCTTC GCCTGTCAGA GAACTCCGGG     1140

GATGAGAACA TGAGTGACGT GACCTTTGAC TCTCTGCCTT CCTCCCCGTC TTCAGCTACA     1200

CCACACAGCC AGAAACTGGA CCACCTCCAT TGGCCAGTGT TTGGTGACCT CGATAACATG     1260

GGCCCTAGAG ACCATGACCG TATGGACAAT CACCGGGACT CTGAGAATAG TGGGGACAGT     1320

GGGTATCCAA GCGAGAAGCG AAGTGACCTG GATGATCCTG AGCCCCGAGA ACACGGCCAC     1380

TCCAACGGCA ACCGAAGGCA TGAATCTGAC GAGGATAGCC TGGGCAGCTC TGGACGGGTC     1440

TGTGTGGAGA CGTGGAACCT GCTCAATCCC TCCCGCCTGC ACCTGCCGAG GCCCTCGGCC     1500

GTGGCCCTAG AAGTGCAGAG GCTAAATGCC CTGGACCTTG GAAGGAAAAT CGGGAAGTCT     1560

GTTTTGGGGA AAGTCCATTT GGCCATGGTG CGATACCACG AGGGCGGGCG CTTCTGCGAG     1620

AAGGATGAGG AGTGGGATCG AGAGTCAGCC ATCTTCCATC TGGAGCATGC AGCTGACCTG     1680

GGAGAACTGG AGGCCATCGT GGGCCTAGGC CTCATGTACT CTCAGCTGCC CCACCACATC     1740

CTGGCTGATG TCTCTCTGAA GGAGACAGAG GAGAACAAGA CAAAAGGCTT TGATTACTTA     1800

CTGAAGGCGG CAGAAGCTGG TGACAGGCAT TCCATGATTT TAGTGGCCCG AGCTTTTGAC     1860

ACTGGCCTGA ACCTCAGCCC AGACAGGTGT CAAGACTGGT CGGAAGCCTT GCACTGGTAC     1920

AACACAGCCC TGGAGACAAC AGACTGCGAT GAAGGCGGGG AGTACGATGG GATACAGGAC     1980

GAGCCCCAGT ACGCACTGCT GGCCAGGGAG GCGGAGATGC TGCTCACCGG GGGATTTGGA     2040

CTGGACAAGA ACCCCCAAAG ATCAGGAGAT TTGTACACCC AGGCAGCTGA GGCAGCAATG     2100

GAAGCCATGA AGGGCCGGCT AGCCAACCAG TACTACGAGA AGGCGGAAGA GGCCTGGGCC     2160

CAGATGGAGG AATAA                                                     2175
```

(2) INFORMATION FOR SEQ ID NO:4:

(i) SEQUENCE CHARACTERISTICS:
        (A) LENGTH: 724 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Mus musculus (xi) SEQUENCE DESCRIPTION: SEQ ID NO:4:

```
Met Ala Asp Glu Asp Leu Ile Phe Cys Leu Glu Gly Val Asp Gly Gly
1               5                  10                  15

Arg Cys Ser Arg Ala Gly His Asn Ala Asp Ser Asp Thr Asp Ser Asp
            20                  25                  30

Asp Asp Glu Gly Tyr Phe Ile Cys Pro Ile Thr Asp Asp His Met Ser
        35                  40                  45
```

-continued

```
Asn Gln Asn Val Ser Ser Lys Val Gln Ser Tyr Tyr Ser Asn Leu Thr
 50                  55                  60
Lys Thr Glu Cys Gly Ser Thr Gly Ser Pro Ala Ser Ser Phe His Phe
 65                  70                  75                  80
Lys Glu Ala Trp Lys His Ala Ile Glu Lys Ala Lys His Met Pro Asp
                 85                  90                  95
Pro Trp Ala Glu Phe His Leu Glu Asp Ile Ala Thr Glu His Ala Thr
                100                 105                 110
Arg His Arg Tyr Asn Ala Val Thr Gly Glu Trp Leu Lys Asp Glu Val
                115                 120                 125
Leu Ile Lys Met Ala Ser Gln Pro Phe Gly Arg Gly Ala Met Arg Glu
130                 135                 140
Cys Phe Arg Thr Lys Lys Leu Ser Asn Phe Leu His Ala Gln Gln Trp
145                 150                 155                 160
Lys Gly Ala Ser Asn Tyr Val Ala Lys Arg Tyr Ile Glu Pro Val Asp
                165                 170                 175
Arg Ser Val Tyr Phe Glu Asp Val Gln Leu Gln Met Glu Ala Lys Leu
                180                 185                 190
Trp Gly Glu Asp Tyr Asn Arg His Lys Pro Pro Lys Gln Val Asp Ile
                195                 200                 205
Met Gln Met Cys Ile Ile Glu Leu Lys Asp Arg Pro Gly Gln Pro Leu
210                 215                 220
Phe His Leu Glu His Tyr Ile Glu Gly Lys Tyr Ile Lys Tyr Asn Ser
225                 230                 235                 240
Asn Ser Gly Phe Val Arg Asp Asp Asn Ile Arg Leu Thr Pro Gln Ala
                245                 250                 255
Phe Ser His Phe Thr Phe Glu Arg Ser Gly His Gln Leu Ile Val Val
                260                 265                 270
Asp Ile Gln Gly Val Gly Asp Leu Tyr Thr Asp Pro Gln Ile His Thr
                275                 280                 285
Glu Lys Gly Thr Asp Phe Gly Asp Gly Asn Leu Gly Val Arg Gly Met
290                 295                 300
Ala Leu Phe Phe Tyr Ser His Ala Cys Asn Arg Ile Cys Gln Ser Met
305                 310                 315                 320
Gly Leu Thr Pro Phe Asp Leu Ser Pro Arg Glu Gln Asp Ala Val Asn
                325                 330                 335
Gln Ser Thr Arg Leu Leu Gln Ser Ala Lys Thr Ile Leu Arg Gly Thr
                340                 345                 350
Glu Glu Lys Cys Gly Ser Pro Arg Ile Arg Thr Leu Ser Ser Ser Arg
                355                 360                 365
Pro Pro Leu Leu Leu Arg Leu Ser Glu Asn Ser Gly Asp Glu Asn Met
370                 375                 380
Ser Asp Val Thr Phe Asp Ser Leu Pro Ser Ser Pro Ser Ser Ala Thr
385                 390                 395                 400
Pro His Ser Gln Lys Leu Asp His Leu His Trp Pro Val Phe Gly Asp
                405                 410                 415
Leu Asp Asn Met Gly Pro Arg Asp His Asp Arg Met Asp Asn His Arg
                420                 425                 430
Asp Ser Glu Asn Ser Gly Asp Ser Gly Tyr Pro Ser Glu Lys Arg Ser
                435                 440                 445
Asp Leu Asp Asp Pro Glu Pro Arg Glu His Gly His Ser Asn Gly Asn
450                 455                 460
```

```
Arg Arg His Glu Ser Asp Glu Asp Ser Leu Gly Ser Ser Gly Arg Val
465                 470                 475                 480

Cys Val Glu Thr Trp Asn Leu Leu Asn Pro Ser Arg Leu His Leu Pro
                485                 490                 495

Arg Pro Ser Ala Val Ala Leu Glu Val Gln Arg Leu Asn Ala Leu Asp
            500                 505                 510

Leu Gly Arg Lys Ile Gly Lys Ser Val Leu Gly Lys Val His Leu Ala
        515                 520                 525

Met Val Arg Tyr His Glu Gly Gly Arg Phe Cys Glu Lys Asp Glu Glu
    530                 535                 540

Trp Asp Arg Glu Ser Ala Ile Phe His Leu Glu His Ala Ala Asp Leu
545                 550                 555                 560

Gly Glu Leu Glu Ala Ile Val Gly Leu Gly Leu Met Tyr Ser Gln Leu
                565                 570                 575

Pro His His Ile Leu Ala Asp Val Ser Leu Lys Glu Thr Glu Glu Asn
            580                 585                 590

Lys Thr Lys Gly Phe Asp Tyr Leu Leu Lys Ala Ala Glu Ala Gly Asp
        595                 600                 605

Arg His Ser Met Ile Leu Val Ala Arg Ala Phe Asp Thr Gly Leu Asn
    610                 615                 620

Leu Ser Pro Asp Arg Cys Gln Asp Trp Ser Glu Ala Leu His Trp Tyr
625                 630                 635                 640

Asn Thr Ala Leu Glu Thr Thr Asp Cys Asp Glu Gly Gly Glu Tyr Asp
                645                 650                 655

Gly Ile Gln Asp Glu Pro Gln Tyr Ala Leu Leu Ala Arg Glu Ala Glu
            660                 665                 670

Met Leu Leu Thr Gly Gly Phe Gly Leu Asp Lys Asn Pro Gln Arg Ser
        675                 680                 685

Gly Asp Leu Tyr Thr Gln Ala Ala Glu Ala Ala Met Glu Ala Met Lys
    690                 695                 700

Gly Arg Leu Ala Asn Gln Tyr Tyr Glu Lys Ala Glu Glu Ala Trp Ala
705                 710                 715                 720

Gln Met Glu Glu (2) INFORMATION FOR SEQ ID NO:5:

(i) SEQUENCE CHARACTERISTICS:
        (A) LENGTH: 3465 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Dictyostelium discoideum (xi) SEQUENCE DESCRIPTION: SEQ ID NO:5:

ATGTTTAATA TAAAAAAGAG AAAAGAGAGT ATAACAGGTA TACCACCAAT AAATGTTAAT      60

AGTCCACAAT CAGTTCCATT GAGTGGAACA TTGCAATCAC CATTGATTAC ACCAAATTCA     120

CCAAATTTTG TTTCACGTCA ATGTCCATTC AAAAAGTTTG GATGTAGTAG TTTTTTAGTT     180

TCAAAGGCAG AGTTTGATAA TCACTTAAAG GATGACGCAC AATTTCATTT ACAATTGGCA     240

GTGGAGAAAT TTGATCATCA ATTTGATTTA CACACACAAT TGATGGCACA TTTTACTGAG     300
```

-continued

```
CAAATGGAGG ATCAATTAGA GAAAACAATG AAGGTCGTAC GTAATCATAC AGATAGTTTA        360

GGCGGTAATG TTCAAACCAA ATTGGATGAA GGCATTGAAA AATGTATGGC TTTTGCTAAA        420

AAGGTTGAAC AACAACAACA ACAATTGGCC AAAAGATTAA TCACTCAACA AATTCAAGAG        480

AAGAAATCAA CCTCTTCACC TTTAGTTAAA GGTGGTATTA GTGGTGGTGG TGGTAGTGGT        540

GGCGATGATT CTTTTGATGG CGCAAATATA TCATCAATGT CAACTAGTAA ACAAGAATTA        600

CAACAAGAAT TACAATCATT ATCAATTAAA ATGAAAAAAG AATTGACAGA ATTATCCGAT        660

GAACTATCAC AAAAATTAGA ACGTTCAACA GGTAATATAG ATATTAAAAT AAAGAGAATC        720

GAAGGTGAAG TTAATGAAAA GATTGATAAA CGTCAATTGG TCTCTACGAT CGATGATTCA        780

ATTGGAAAGA AAACAGATTC CATCGGTTAT ACATTGGAGA GTTCAATCAT TAAAAAGGTT        840

GAAGAGAAAG AGAAAAAGAA ATCCGAACAA AATCAACTTC TCTTTGATTC AAAGATTGAA        900

TCCTTAAAAG ATAAGATTAA AATCATTGAA ACTCAACAAT GGATACTTC ATCAGAGGTT         960

AGAAAATTGA AATTAGAAAG TACAAGTAGT GGAAATTTAA TGGCAGGTCT TAATGGTACC       1020

TCTGGTAGAC CTTCATCATC TTCTCACTTT ATTCCATCCT CTGTTTCTGC CGCTGCTAAC       1080

AATATCAACA AGAATGAAAT CATGGAAGAG GTTAAAAAGG TAGAAGAGAA ACTTCAAAAG       1140

AAAATTCGTG AAGAGATTGA TAATACAAAA GCTGAACTCT CAAAGGTTGA ACGTTCCGTT       1200

AAAGATAATC GTAGTGAAAT TGAAGGTTTG GAAAAAGATT GTAAGAATCA ATTCGATAAA       1260

CAAGACAATA AGATCAAACA AGTTGAGGAT GATTTGAAAA AGAGTGATTC ATTACTTTTG       1320

TTAATGCAAA ATAACCTCAA GAAATATAAT GAATTTGTTG ATAGAGAACG TGATCGTGAA       1380

AGTGAACGTT TGAAACTTCA AGATTCTATC AAACGTTTAG AACAAAATCA AAAGAAAATC       1440

GAAGCTGAAA TTCAAGAAGG TAATGAACAA GTTGAACGTG TTTTACGTGA GGAAGCTTCA       1500

ATCTCACCAA TTAGTTCAGT TCCAAAATCA CCAATCACAA CCAAACGTTC ATCGATTATT       1560

TTAAATTCAC CACCAATGAC TTCACAACAA TCATCACCAA AGATTCAAGA TCTTCTCTCA       1620

AGTAGTGGTA GTAGTAGTGT TAGTGGTATA AATATTTCCT CTGAAACCGG TGAAATGGGT       1680

ATTCTTTGGG AATTTGATCC AATCATTAAC AAATGGATTA GATTATCAAT GAAGCTAAAG       1740

GTAGAAAGAA AACCATTTGC AGAGGGTGCT CTTAGAGAGG CTTATCATAC CGTTTCATTG       1800

GGTGTTGGAA CCGATGAAAA TTATCCATTA GGTACAACCA CCAAATTATT CCCACCAATT       1860

GAAATGATTT CACCAATTTC AAAGAATAAT GAGGCAATGA CTCAATTGAA GAATGGTACA       1920

AAATTTGTTT TGAAACTCTA CAAAAAGGAA GCTGAACAAC AAGCTAGCAG AGAATTATAC       1980

TTTGAAGATG TTAAAATGCA AATGGTCTGT AGAGATTGGG GTAATAAATT CAATCAAAAG       2040

AAACCACCAA AGAAAATTGA ATTCCTTATG TCTTGGGTTG TAGAGTTAAT CGATAGATCT       2100

CCTTCTTCCA ATGGTCAACC AATACTTTGT TCCATTGAAC CATTATTGGT TGGTGAATTC       2160

AAAAAGAATA ATTCAAATTA TGGTGCAGTT TTAACCAATC GTTCAACTCC ACAAGCATTC       2220

TCTCATTTCA CCTATGAACT CTCAAATAAA CAAATGATCG TTGTCGATAT TCAAGGTGTT       2280

GATGATCTTT ACACTGATCC TCAAATTCAT ACACCCGATG GTAAAGGATT TGGTCTTGGT       2340

AATCTTGGTA AAGCAGGTAT CAATAAATTC ATCACCACTC ACAAATGTAA TGCTGTTTGT       2400

GCTCTTTTAG ATTTAGATGT TAAATTGGGT GGTGTACTAT CTGGAAATAA TAAGAAACAA       2460

CTTCAACAAG GTACTATGGT TATGCCAGAT ATTCTCCCAG AACTTATGCC ATCTGATAAC       2520

ACCATTAAAG TGGGTGCAAA ACAACTTCCA AAAGCTGAAT TCTCAAAGAA AGATCTCAAA       2580

TGTGTTAGCA CCATTCAAAG TTTCCGTGAA CGTGTTAACT CGATCGCATT CTTTGATAAT       2640
```

-continued

```
CAAAAGTTAT TATGCGCTGG TTATGGTGAT GGTACCTATA GAGTTTTCGA TGTCAATGAC      2700

AATTGGAAAT GTTTATACAC TGTCAATGGT CATAGAAAAT CAATTGAAAG TATCGCTTGT      2760

AATAGTAATT ACATTTTCAC TTCATCACCT GATAACACCA TCAAAGTTCA TATCATTCGT      2820

AGTGGTAACA CCAAATGTAT AGAGACATTG GTTGGTCACA CTGGTGAAGT TAATTGTGTC      2880

GTGGCCAATG AAAAATATCT TTTCAGTTGT AGTTATGATA AAACTATCAA GGTTTGGGAT      2940

TTGTCAACCT TTAAAGAAAT TAAATCATTT GAGGGTGTTC ATACAAAGTA CATTAAAACA      3000

TTGGCTTTGA GTGGACGTTA TCTTTTTAGT GGTGGTAACG ATCAAATCAT TTACGTTTGG      3060

GATACTGAAA CACTTAGTAT GCTTTTCAAT ATGCAAGGTC ATGAAGATTG GGTACTCTCT      3120

CTTCATTGTA CCGCTAGTTA TCTTTTCTCA ACCTCAAAAG ATAATGTCAT CAAGATTTGG      3180

GATCTCTCAA ATTTCAGTTG TATCGATACT CTAAAAGGTC ATTGGAATTC TGTCTCAAGT      3240

TGTGTCGTAA AAGATCGTTA TCTATACAGT GGTTCTGAAG ATAATTCAAT CAAAGTTTGG      3300

GATCTCGATA CACTTGAATG TGTTTACACC ATTCCAAAAT CTCATTCTTT GGGTGTAAAA      3360

TGTTTAATGG TTTTCAATAA TCAAATCATT TCTGCTGCTT TCGATGGTTC AATTAAAGTT      3420

TGGGAATGGC AATCGAAATA ATCTTTGTAA ATTTTTGTTA AAAAA                     3465
```

(2) INFORMATION FOR SEQ ID NO:6:

(i) SEQUENCE CHARACTERISTICS:
        (A) LENGTH: 1146 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Dictyostelium discoideum (xi) SEQUENCE DESCRIPTION: SEQ ID NO:6:

```
Met Phe Asn Ile Lys Lys Arg Lys Glu Ser Ile Thr Gly Ile Pro Pro
1               5                   10                  15

Ile Asn Val Asn Ser Pro Gln Ser Val Pro Leu Ser Gly Thr Leu Gln
            20                  25                  30

Ser Pro Leu Ile Thr Pro Asn Ser Pro Asn Phe Val Ser Arg Gln Cys
        35                  40                  45

Pro Phe Lys Lys Phe Gly Cys Ser Ser Phe Leu Val Ser Lys Ala Glu
    50                  55                  60

Phe Asp Asn His Leu Lys Asp Asp Ala Gln Phe His Leu Gln Leu Ala
65                  70                  75                  80

Val Glu Lys Phe Asp His Gln Phe Asp Leu His Thr Gln Leu Met Ala
                85                  90                  95

His Phe Thr Glu Gln Met Glu Asp Gln Leu Glu Lys Thr Met Lys Val
            100                 105                 110

Val Arg Asn His Thr Asp Ser Leu Gly Gly Asn Val Gln Thr Lys Leu
        115                 120                 125

Asp Glu Gly Ile Glu Lys Cys Met Ala Phe Ala Lys Val Glu Gln
    130                 135                 140

Gln Gln Gln Gln Leu Ala Lys Arg Leu Ile Thr Gln Ile Gln Glu
145                 150                 155                 160

Lys Lys Ser Thr Ser Ser Pro Leu Val Lys Gly Gly Ile Ser Gly Gly
                165                 170                 175
```

```
Gly Gly Ser Gly Gly Asp Asp Ser Phe Asp Gly Ala Asn Ile Ser Ser
            180                 185                 190

Met Ser Thr Ser Lys Gln Glu Leu Gln Gln Glu Leu Gln Ser Leu Ser
            195                 200                 205

Ile Lys Met Lys Lys Glu Leu Thr Glu Leu Ser Asp Glu Leu Ser Gln
210                 215                 220

Lys Leu Glu Arg Ser Thr Gly Asn Ile Asp Ile Lys Ile Lys Arg Ile
225                 230                 235                 240

Glu Gly Glu Val Asn Glu Lys Ile Asp Lys Arg Gln Leu Val Ser Thr
                245                 250                 255

Ile Asp Asp Ser Ile Gly Lys Lys Thr Asp Ser Ile Gly Tyr Thr Leu
            260                 265                 270

Glu Ser Ser Ile Ile Lys Lys Val Glu Glu Lys Glu Lys Lys Lys Ser
            275                 280                 285

Glu Gln Asn Gln Leu Leu Phe Asp Ser Lys Ile Glu Ser Leu Lys Asp
            290                 295                 300

Lys Ile Lys Ile Ile Glu Thr Gln Gln Leu Asp Thr Ser Ser Glu Val
305                 310                 315                 320

Arg Lys Leu Lys Leu Glu Ser Thr Ser Ser Gly Asn Leu Met Ala Gly
                325                 330                 335

Leu Asn Gly Thr Ser Gly Arg Pro Ser Ser Ser His Phe Ile Pro
            340                 345                 350

Ser Ser Val Ser Ala Ala Ala Asn Asn Ile Asn Lys Asn Glu Ile Met
            355                 360                 365

Glu Glu Val Lys Lys Val Glu Glu Lys Leu Gln Lys Lys Ile Arg Glu
            370                 375                 380

Glu Ile Asp Asn Thr Lys Ala Glu Leu Ser Lys Val Glu Arg Ser Val
385                 390                 395                 400

Lys Asp Asn Arg Ser Glu Ile Glu Gly Leu Glu Lys Asp Cys Lys Asn
                405                 410                 415

Gln Phe Asp Lys Gln Asp Asn Lys Ile Lys Gln Val Glu Asp Asp Leu
            420                 425                 430

Lys Lys Ser Asp Ser Leu Leu Leu Met Gln Asn Asn Leu Lys Lys
435                 440                 445

Tyr Asn Glu Phe Val Asp Arg Gly Arg Asp Arg Glu Ser Glu Arg Leu
450                 455                 460

Lys Leu Gln Asp Ser Ile Lys Arg Leu Glu Gln Asn Gln Lys Lys Ile
465                 470                 475                 480

Glu Ala Glu Ile Gln Glu Gly Asn Glu Gln Val Glu Arg Val Leu Arg
            485                 490                 495

Glu Glu Ala Ser Ile Ser Pro Ile Ser Ser Val Pro Lys Ser Pro Ile
            500                 505                 510

Thr Thr Lys Arg Ser Ser Ile Ile Leu Asn Ser Pro Pro Met Thr Ser
            515                 520                 525

Gln Gln Ser Ser Pro Lys Ile Gln Asp Leu Leu Ser Ser Gly Ser
            530                 535                 540

Ser Ser Val Ser Gly Ile Asn Ile Ser Ser Glu Thr Gly Glu Met Gly
545                 550                 555                 560

Ile Leu Trp Glu Phe Asp Pro Ile Ile Asn Lys Trp Ile Arg Leu Ser
                565                 570                 575

Met Lys Leu Lys Val Glu Arg Lys Pro Phe Ala Glu Gly Ala Leu Arg
            580                 585                 590
```

```
Glu Ala Tyr His Thr Val Ser Leu Gly Val Gly Thr Asp Glu Asn Tyr
            595                 600                 605
Pro Leu Gly Thr Thr Thr Lys Leu Phe Pro Pro Ile Glu Met Ile Ser
            610                 615                 620
Pro Ile Ser Lys Asn Asn Glu Ala Met Thr Gln Leu Lys Asn Gly Thr
625                 630                 635                 640
Lys Phe Val Leu Lys Leu Tyr Lys Lys Glu Ala Glu Gln Gln Ala Ser
            645                 650                 655
Arg Glu Leu Tyr Phe Glu Asp Val Lys Met Gln Met Val Cys Arg Asp
            660                 665                 670
Trp Gly Asn Lys Phe Asn Gln Lys Lys Pro Pro Lys Lys Ile Glu Phe
            675                 680                 685
Leu Met Ser Trp Val Val Glu Leu Ile Asp Arg Ser Pro Ser Ser Asn
            690                 695                 700
Gly Gln Pro Ile Leu Cys Ser Ile Glu Pro Leu Leu Val Gly Glu Phe
705                 710                 715                 720
Lys Lys Asn Asn Ser Asn Tyr Gly Ala Val Leu Thr Asn Arg Ser Thr
            725                 730                 735
Pro Gln Ala Phe Ser His Phe Thr Tyr Glu Leu Ser Asn Lys Gln Met
            740                 745                 750
Ile Val Val Asp Ile Gln Gly Val Asp Asp Leu Tyr Thr Asp Pro Gln
            755                 760                 765
Ile His Thr Pro Asp Gly Lys Gly Phe Gly Leu Gly Asn Leu Gly Lys
            770                 775                 780
Ala Gly Ile Asn Lys Phe Ile Thr Thr His Lys Cys Asn Ala Val Cys
785                 790                 795                 800
Ala Leu Leu Asp Leu Asp Val Lys Leu Gly Gly Val Leu Ser Gly Asn
            805                 810                 815
Asn Lys Lys Gln Leu Gln Gln Gly Thr Met Val Met Pro Asp Ile Leu
            820                 825                 830
Pro Glu Leu Met Pro Ser Asp Asn Thr Ile Lys Val Gly Ala Lys Gln
            835                 840                 845
Leu Pro Lys Ala Glu Phe Ser Lys Lys Asp Leu Lys Cys Val Ser Thr
850                 855                 860
Ile Gln Ser Phe Arg Glu Arg Val Asn Ser Ile Ala Phe Phe Asp Asn
865                 870                 875                 880
Gln Lys Leu Leu Cys Ala Gly Tyr Gly Asp Gly Thr Tyr Arg Val Phe
            885                 890                 895
Asp Val Asn Asp Asn Trp Lys Cys Leu Tyr Thr Val Asn Gly His Arg
            900                 905                 910
Lys Ser Ile Glu Ser Ile Ala Cys Asn Ser Asn Tyr Ile Phe Thr Ser
            915                 920                 925
Ser Pro Asp Asn Thr Ile Lys Val His Ile Ile Arg Ser Gly Asn Thr
            930                 935                 940
Lys Cys Ile Glu Thr Leu Val Gly His Thr Gly Glu Val Asn Cys Val
945                 950                 955                 960
Val Ala Asn Glu Lys Tyr Leu Phe Ser Cys Ser Tyr Asp Lys Thr Ile
            965                 970                 975
Lys Val Trp Asp Leu Ser Thr Phe Lys Glu Ile Lys Ser Phe Glu Gly
            980                 985                 990
Val His Thr Lys Tyr Ile Lys Thr Leu Ala Leu Ser Gly Arg Tyr Leu
            995                 1000                1005
```

```
Phe Ser Gly Gly Asn Asp Gln Ile Ile Tyr Val Trp Asp Thr Glu Thr
        1010                1015                1020
Leu Ser Met Leu Phe Asn Met Gln Gly His Glu Asp Trp Val Leu Ser
1025            1030                1035                1040
Leu His Cys Thr Ala Ser Tyr Leu Phe Ser Thr Ser Lys Asp Asn Val
                1045                1050                1055
Ile Lys Ile Trp Asp Leu Ser Asn Phe Ser Cys Ile Asp Thr Leu Lys
        1060                1065                1070
Gly His Trp Asn Ser Val Ser Ser Cys Val Val Lys Asp Arg Tyr Leu
            1075                1080                1085
Tyr Ser Gly Ser Glu Asp Asn Ser Ile Lys Val Trp Asp Leu Asp Thr
        1090                1095                1100
Leu Glu Cys Val Tyr Thr Ile Pro Lys Ser His Ser Leu Gly Val Lys
1105            1110                1115                1120
Cys Leu Met Val Phe Asn Asn Gln Ile Ile Ser Ala Ala Phe Asp Gly
                1125                1130                1135
Ser Ile Lys Val Trp Glu Trp Gln Ser Lys
            1140                1145
```

(2) INFORMATION FOR SEQ ID NO:7:

(i) SEQUENCE CHARACTERISTICS:
        (A) LENGTH: 2237 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Dictyostelium discoideum (xi) SEQUENCE DESCRIPTION: SEQ ID NO:7:

```
ATAAGAAGAT AGAAGATGAT ATTTAAAGTT TGGTTTTCAT ATGAAGATGA GGAAGTGGAA      60

CTATCAGAAT TAACAAATGA TACAACAGTG TCAGCAATTA GAAAGATCTT ACATGAAGGT     120

AAAATATTTA GATTTCCATA TGGTACATCT CAAACAGACT TGCAAATTGG AAAGATGTTA     180

CCATCTGGTA GTGGTGGAGG TGCAACTGCA GACAGCAAAT TTGAGAAGTT TAAAGCACGT     240

AATACATTAG CAGATATTCA ATATAAAGTT GGTGATACAT TATATGTTAG AGTTAAAAAA     300

AGTAAACCAA CAAATGATTC ATTATTACCA ACATTAAATA TAGCATTTTT AGATGGATCA     360

GAACGTGCAA TTAAATGGGA ATATGACCCA TATACTACAA CTGCTCAATG GACCTGTACA     420

GCAACATTAG TCAAAGTTGA ACCAGTACCA TTTGCTGAAG GTGCATTTAG GAAAGCTTAT     480

CATACATTGG ATTTAAGTAA ATCTGGTGCA AGTGGAAGAT ATGTATCAAA GATTGGTAAA     540

AAACCAACAC CAAGACCATC ATATTTTGAA GATGTAAAGA TGCAAATGAT AGCAAAGAAA     600

TGGGCAGATA AATATAATTC ATTTAAACCT CCAAAAAAGA TTGAATTTTT ACAATCATGC     660

GTTTTAGAGT TTGTAGATAG AACATCATCA GATTTAATTT GTGGAGCAGA ACCATATGTA     720

GAAGGACAAT ATAGAAAGTA TAATAATAAT AGTGGATTCG TTAGTAATGA TGAAAGAAAT     780

ACACCACAAT CATTCTCTCA TTTCACATAT GAACATTCAA ATCATCAATT ATTGATTATA     840

GATATTCAAG GTGTTGGTGA TCACTATACA GACCCACAAA TTCATACCTA TGATGGTGTT     900

GGTTTTGGTA TTGGTAATTT GGGTCAAAAA GGTTTTGAAA AGTTTTTAGA TACTCATAAA     960
```

-continued

```
TGTAATGCAA TTTGCCAATA TTTAAATTTA CAATCAATTA ATCCAAAATC TGAAAAAAGT    1020

GATTGTGGTA CTGTACCAAG ACCAGATTTA ATTTTCCCTG ATACATCTGA AAGAGATAAT    1080

AATAATAATA ATAATAATAA TAATAATAAT AATAATAATA ATAATAATAA TAATAGTAAT    1140

AATAATAATA ATAACAATAG TAGTATTTCA AAATCATTAG TTGAAATTTC AAGTGGTAGT    1200

AAAGAAAGAA ATGATAGAGA TTCGCCAAGT AGACAATTAT TTGTTTCAAA TGATGGTAAT    1260

ACATTAAATA CAAATAAAGA GAGATCAAAA TCAAATCAA TAGATTTAGA AAACCAGAA      1320

ATTTTAATAA ATAATAAGAA AAAGAGAGT ATAAATTTGG AAACGATAAA ATTAATTGAA     1380

ACTATTAAAG GATATCATGT TACAAGTCAT TTATGTATTT GTGATAATTT ATTATTTACA    1440

GGATGTTCAG ATAATTCAAT TAGAGTGTAT GATTATAAGA GTCAAAATAT GGAATGTGTT    1500

CAAACCTTGA AAGGTCATGA AGGTCCAGTT GAATCAATTT GTTATAATGA TCAATATTTG    1560

TTTAGTGGTT CATCAGATCA TTCAATTAAA GTTTGGGATT TAAAGAAATT AAGATGTATT    1620

TTTACTTTGG AGGGTCATGA TAAACCTGTC CATACGGTTC TATTGAATGA TAAATATTTG    1680

TTTAGTGGTT CCTCTGACAA AACTATCAAA GTTTGGGATT TGAAAACTTT GGAATGTAAA    1740

TATACCCTTG AAAGTCATGC CAGAGCCGTC AAAACACTTT GTATATCTGG TCAATATTTA    1800

TTTAGTGGTT CAAATGATAA AACTATCAAG GTTTGGGATT TGAAAACTTT TCGTTGTAAC    1860

TACACTCTAA AAGGTCATAC TAAATGGGTC ACCACTATCT GTATATTAGG TACCAATCTC    1920

TACAGTGGCT CCTATGATAA AACTATAAGA GTTTGGAATT TAAAGAGTTT AGAATGTTCC    1980

GCTACTTTAA GAGGCCATGA TAGATGGGTT GAACATATGG TAATTTGTGA TAAATTATTA    2040

TTTACTGCTA GTGACGATAA TACAATTAAA ATTTGGGATT TAGAAACATT AAGATGTAAT    2100

ACAACTTTGG AAGGACATAA TGCAACCGTT CAATGTTTAG CAGTTTGGGA AGATAAAAAA    2160

TGTGTTATTA GTTGTAGTCA TGATCAAAGT ATTAGAGTTT GGGGTTGGAA TTAATTTAAA    2220

ATAAAAAAAA AAAACAT                                                  2237
```

(2) INFORMATION FOR SEQ ID NO:8:

(i) SEQUENCE CHARACTERISTICS:
        (A) LENGTH: 732 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Dictyostelium discoideum (xi) SEQUENCE DESCRIPTION: SEQ ID NO:8:

```
Met Ile Phe Lys Val Trp Phe Ser Tyr Glu Asp Glu Val Glu Leu
1               5                  10                  15

Ser Glu Leu Thr Asn Asp Thr Thr Val Ser Ala Ile Arg Lys Ile Leu
            20                  25                  30

His Glu Gly Lys Ile Phe Arg Phe Pro Tyr Gly Thr Ser Gln Thr Asp
        35                  40                  45

Leu Gln Ile Gly Lys Met Leu Pro Ser Gly Ser Gly Gly Ala Thr
    50                  55                  60

Ala Asp Ser Lys Phe Glu Lys Phe Lys Ala Arg Asn Thr Leu Ala Asp
65                  70                  75                  80

Ile Gln Tyr Lys Val Gly Asp Thr Leu Tyr Val Arg Val Lys Lys Ser
```

-continued

```
                85                  90                  95
Lys Pro Thr Asn Asp Ser Leu Leu Pro Thr Leu Asn Ile Ala Phe Leu
            100                 105                 110
Asp Gly Ser Glu Arg Ala Ile Lys Trp Glu Tyr Asp Pro Tyr Thr Thr
            115                 120                 125
Thr Ala Gln Trp Thr Cys Thr Ala Thr Leu Val Lys Val Glu Pro Val
            130                 135                 140
Pro Phe Ala Glu Gly Ala Phe Arg Lys Ala Tyr His Thr Leu Asp Leu
145                 150                 155                 160
Ser Lys Ser Gly Ala Ser Gly Arg Tyr Val Ser Lys Ile Gly Lys Lys
                165                 170                 175
Pro Thr Pro Arg Pro Ser Tyr Phe Glu Asp Val Lys Met Gln Met Ile
            180                 185                 190
Ala Lys Lys Trp Ala Asp Lys Tyr Asn Ser Phe Lys Pro Pro Lys Lys
            195                 200                 205
Ile Glu Phe Leu Gln Ser Cys Val Leu Glu Phe Val Asp Arg Thr Ser
    210                 215                 220
Ser Asp Leu Ile Cys Gly Ala Glu Pro Tyr Val Glu Gly Gln Tyr Arg
225                 230                 235                 240
Lys Tyr Asn Asn Asn Ser Gly Phe Val Ser Asn Asp Glu Arg Asn Thr
                245                 250                 255
Pro Gln Ser Phe Ser His Phe Thr Tyr Glu His Ser Asn His Gln Leu
            260                 265                 270
Leu Ile Ile Asp Ile Gln Gly Val Gly Asp His Tyr Thr Asp Pro Gln
            275                 280                 285
Ile His Thr Tyr Asp Gly Val Gly Phe Gly Ile Gly Asn Leu Gly Gln
        290                 295                 300
Lys Gly Phe Glu Lys Phe Leu Asp Thr His Lys Cys Asn Ala Ile Cys
305                 310                 315                 320
Gln Tyr Leu Asn Leu Gln Ser Ile Asn Pro Lys Ser Glu Lys Ser Asp
                325                 330                 335
Cys Gly Thr Val Pro Arg Pro Asp Leu Ile Phe Pro Asp Thr Ser Glu
            340                 345                 350
Arg Asp Asn Asn Asn Asn Asn Asn Asn Asn Asn Asn Asn Asn Asn Asn
            355                 360                 365
Asn Asn Asn Asn Ser Asn Asn Asn Asn Asn Asn Ser Ser Ile
    370                 375                 380
Ser Lys Ser Leu Val Glu Ile Ser Ser Gly Ser Lys Glu Arg Asn Asp
385                 390                 395                 400
Arg Asp Ser Pro Ser Arg Gln Leu Phe Val Ser Asn Asp Gly Asn Thr
            405                 410                 415
Leu Asn Thr Asn Lys Glu Arg Ser Lys Ser Lys Ser Ile Asp Leu Glu
            420                 425                 430
Lys Pro Glu Ile Leu Ile Asn Lys Lys Lys Glu Ser Ile Asn Leu
            435                 440                 445
Glu Thr Ile Lys Leu Ile Glu Thr Ile Lys Gly Tyr His Val Thr Ser
    450                 455                 460
His Leu Cys Ile Cys Asp Asn Leu Leu Phe Thr Gly Cys Ser Asp Asn
465                 470                 475                 480
Ser Ile Arg Val Tyr Asp Tyr Lys Ser Gln Asn Met Glu Cys Val Gln
                485                 490                 495
Thr Leu Lys Gly His Glu Gly Pro Val Glu Ser Ile Cys Tyr Asn Asp
```

-continued

```
                    500             505             510
    Gln Tyr Leu Phe Ser Gly Ser Ser Asp His Ser Ile Lys Val Trp Asp
            515             520             525
    Leu Lys Lys Leu Arg Cys Ile Phe Thr Leu Glu Gly His Asp Lys Pro
            530             535             540
    Val His Thr Val Leu Leu Asn Asp Lys Tyr Leu Phe Ser Gly Ser Ser
    545             550             555             560
    Asp Lys Thr Ile Lys Val Trp Asp Leu Lys Thr Leu Glu Cys Lys Tyr
                    565             570             575
    Thr Leu Glu Ser His Ala Arg Ala Val Lys Thr Leu Cys Ile Ser Gly
                580             585             590
    Gln Tyr Leu Phe Ser Gly Ser Asn Asp Lys Thr Ile Lys Val Trp Asp
            595             600             605
    Leu Lys Thr Phe Arg Cys Asn Tyr Thr Leu Lys Gly His Thr Lys Trp
            610             615             620
    Val Thr Thr Ile Cys Ile Leu Gly Thr Asn Leu Tyr Ser Gly Ser Tyr
    625             630             635             640
    Asp Lys Thr Ile Arg Val Trp Asn Leu Lys Ser Leu Glu Cys Ser Ala
                    645             650             655
    Thr Leu Arg Gly His Asp Arg Trp Val Glu His Met Val Ile Cys Asp
                660             665             670
    Lys Leu Leu Phe Thr Ala Ser Asp Asp Asn Thr Ile Lys Ile Trp Asp
            675             680             685
    Leu Glu Thr Leu Arg Cys Asn Thr Thr Leu Gly His Asn Ala Thr
            690             695             700
    Val Gln Cys Leu Ala Val Trp Glu Asp Lys Lys Cys Val Ile Ser Cys
    705             710             715             720
    Ser His Asp Gln Ser Ile Arg Val Trp Gly Trp Asn
                    725             730
```

(2) INFORMATION FOR SEQ ID NO:9:

(i) SEQUENCE CHARACTERISTICS:
        (A) LENGTH: 2307 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: C. elegans (xi) SEQUENCE DESCRIPTION: SEQ ID NO:9:

```
ATGACGATCG ACACAACAAA TGAGAGCGAC AATAGTCCAA CTAACTCACC AGGATTGGAG    60

GCCTCGGCTC GGACATTCTC GCTCAATGCG TCAAAAATGG TTCGGATAAC CGACGACTAC   120

GCAGATGAAG TGTTCATTGA ACAGAATGAT GTCGTTATCG AGAAGCCTCG TATGGATCCT   180

CTCCACGTTA GAAAACTTAT GGAGACATGG CGCAAGGCTG CTCGCCGAGC AAGAACAAAC   240

TATATAGATC CATGGGATGA GTTCAACATC CACGAGTATC CAGTACAACG AGCTAAACGA   300

TATAGGTATT CTGCAATCAG AAAGCAATGG ACAGAGGATA TAGTCGATGT GAGACTTCAT   360

CCGGACAGTT TTGCACGTGG AGCCATGCGA GAATGCTACC GACTCAAAAA GTGCTCCAAG   420

CACGGAACAA GTCAAGATTG GAGCAGCAAC TATGTCGCAA AAAGATACAT TTGTCAAGTC   480
```

```
GATCGTAGAG TTCTTTTCGA TGATGTCAGA CTTCAGATGG ATGCCAAATT ATGGGCTGAA    540

GAATATAATC GGTATAATCC ACCGAAGAAA ATTGATATTG TTCAAATGTG TGTCATTGAG    600

ATGATTGATG TAAAAGGTTC TCCACTCTAT CATTTGGAGC ATTTCATCGA GGGAAAATAT    660

ATAAAATACA ATTCAAACTC AGGATTTGTA TCAAATGCAG CTCGTCTTAC ACCACAAGCA    720

TTTTCTCACT TCACCTTCGA ACGTTCTGGT CATCAAATGA TGGTTGTCGA TATTCAAGGA    780

GTTGGTGATC TTTACACAGA TCCTCAGATT CATACAGTTG TGGGAACTGA TTATGGAGAT    840

GGAAACCTCG GAACTCGTGG AATGGCTCTT TTCTTCCATT CACACAGATG TAACGATATT    900

TGTGAGACAA TGGATCTATC AAATTTCGAA CTTTCGCCAC CTGAAATCGA GGCTACCGAA    960

GTTGCGATGG AAGTAGCTGC AAAGCAGAAA AAGTCATGCA TAGTTCCTCC AACTGTGTTC   1020

GAAGCAAGAA GAAATCGAAT TTCAAGTGAA TGTGTACATG TCGAGCATGG TATTTCGATG   1080

GATCAATTGA GAAAAGGAA GACGTTGAAT CAATCGTCAA CCGATTTGTC AGCAAAGAGT   1140

CACAACGAAG ACTGTGTATG TCCTGAGTGT ATTCCAGTTG TTGAGCAACT CTGTGAGCCT   1200

TGCTCCGAAG ATGAAGAGGA CGAAGAAGAA GACTATCCAA GAAGTGAAAA AGTGGAAAT   1260

AGTCAGAAAA GTCGACGTAG TAGAATGAGC ATTTCAACGA GATCTTCTGG CGATGAATCA   1320

GCATCTCGTC CTAGAAAATG CGGATTTGTA GATTTAAACT CACTTCGTCA GAGACATGAT   1380

AGCTTCAGAA GTTCTGTTGG GACATATTCT ATGAATAGTT CTAGACAAAC CAGAGACACT   1440

GAAAAGGATG AATTCTGGAA GGTTCTTCGA AAACAATCAG TTCCAGCAAA CATTCTATCA   1500

CTTCAACTTC AACAAATGGC TGCTAACCTG GAAAATGATG AAGACGTACC ACAAGTCACC   1560

GGGCATCAGT TCTCTGTCCT CGGTCAGATT CATATTGATC TCTCACGATA TCATGAGCTC   1620

GGGCGGTTCG TAGAAGTTGA TTCAGAACAT AAGGAAATGC TTGAGGGAAG TGAAAATGAC   1680

GCTCGTGTAC CAATCAAATA CGACAAGCAG TCTGCAATTT TCCATTTGGA TATCGCTCGG   1740

AAGTGTGGAA TCCTTGAGGC TGTGCTAACA TCGGCTCATA TTGTTCTCGG ATTACCACAT   1800

GAATTGTTGA AGAAGTCAC CGTTGATGAT CTGTTTCCTA ATGGGTTTGG AGAACAGGAA   1860

AATGGAATTC GAGCTGATAA AGGACAAAAA CCTTGTGACC TAGAAGAGTT CGGCTCCGAT   1920

CTGATGGAAA TTGCTGCAGA GATGGGTGAT AAGGGTGCAA TGCTGTACAT GGCACACGCT   1980

TATGAAACTG GTCAGCATCT CGGACCGAAT CGAAGAACGG ATTATAAGAA ATCGATTGAT   2040

TGGTATCAAC GCGTCGTTGG ATTCCAAGAA GAAGAAGAAC TTGACTCTGA TTGTGGAAAA   2100

ACGACATTCT CCTCATTTGC TCCACTGACT CGTCACGAGA TTCTAGCCAA AATGGCTGAA   2160

ATGTACAAAG AGGGAGGTTA TGGCCTGAAT CAAGACTTCG AACGAGCATA TGGTCTATTC   2220

AATGAAGCTG CTGAAGCAGC AATGGAAGCA ATGAATGGAA AGCTCGCAAA TAAATACTAT   2280

GAAAAAGCGG AAATGTGTGG AGAATGA                                      2307
```

(2) INFORMATION FOR SEQ ID NO:10:

(i) SEQUENCE CHARACTERISTICS:
    (A) LENGTH: 768 amino acids
    (B) TYPE: amino acid
    (C) STRANDEDNESS: single
    (D) TOPOLOGY: linear (ii) MOLECULE TYPE: protein (iii) HYPOTHETICAL: NO (vi) ORIGINAL SOURCE:
    (A) ORGANISM: C. elegans -continued (xi) SEQUENCE DESCRIPTION: SEQ ID NO:10:

| | | | | | | | | | | | | | | |
|---|---|---|---|---|---|---|---|---|---|---|---|---|---|---|
| Met | Thr | Ile | Asp | Thr | Thr | Asn | Glu | Ser | Asp | Asn | Ser | Pro | Thr | Asn | Ser |
| 1 | | | | 5 | | | | | 10 | | | | | 15 | |
| Pro | Gly | Leu | Glu | Ala | Ser | Ala | Arg | Thr | Phe | Ser | Leu | Asn | Ala | Ser | Lys |
| | | | 20 | | | | | 25 | | | | | 30 | | |
| Met | Val | Arg | Ile | Thr | Asp | Asp | Tyr | Ala | Asp | Glu | Val | Phe | Ile | Glu | Gln |
| | | 35 | | | | | 40 | | | | | 45 | | | |
| Asn | Asp | Val | Val | Ile | Glu | Lys | Pro | Arg | Met | Asp | Pro | Leu | His | Val | Arg |
| 50 | | | | | 55 | | | | | 60 | | | | | |
| Lys | Leu | Met | Glu | Thr | Trp | Arg | Lys | Ala | Arg | Arg | Ala | Arg | Thr | Asn | |
| 65 | | | | 70 | | | | | 75 | | | | | 80 | |
| Tyr | Ile | Asp | Pro | Trp | Asp | Glu | Phe | Asn | Ile | His | Glu | Tyr | Pro | Val | Gln |
| | | | 85 | | | | | 90 | | | | | 95 | | |
| Arg | Ala | Lys | Arg | Tyr | Arg | Tyr | Ser | Ala | Ile | Arg | Lys | Gln | Trp | Thr | Glu |
| | | | 100 | | | | | 105 | | | | | 110 | | |
| Asp | Ile | Val | Asp | Val | Arg | Leu | His | Pro | Asp | Ser | Phe | Ala | Arg | Gly | Ala |
| | | | 115 | | | | | 120 | | | | | 125 | | |
| Met | Arg | Glu | Cys | Tyr | Arg | Leu | Lys | Lys | Cys | Ser | Lys | His | Gly | Thr | Ser |
| | | 130 | | | | | 135 | | | | | 140 | | | |
| Gln | Asp | Trp | Ser | Ser | Asn | Tyr | Val | Ala | Lys | Arg | Tyr | Ile | Cys | Gln | Val |
| 145 | | | | | 150 | | | | | 155 | | | | | 160 |
| Asp | Arg | Arg | Val | Leu | Phe | Asp | Asp | Val | Arg | Leu | Gln | Met | Asp | Ala | Lys |
| | | | | 165 | | | | | 170 | | | | | 175 | |
| Leu | Trp | Ala | Glu | Glu | Tyr | Asn | Arg | Tyr | Asn | Pro | Pro | Lys | Lys | Ile | Asp |
| | | | 180 | | | | | 185 | | | | | 190 | | |
| Ile | Val | Gln | Met | Cys | Val | Ile | Glu | Met | Ile | Asp | Val | Lys | Gly | Ser | Pro |
| | | | 195 | | | | | 200 | | | | | 205 | | |
| Leu | Tyr | His | Leu | Glu | His | Phe | Ile | Glu | Gly | Lys | Tyr | Ile | Lys | Tyr | Asn |
| | | 210 | | | | | 215 | | | | | 220 | | | |
| Ser | Asn | Ser | Gly | Phe | Val | Ser | Asn | Ala | Ala | Arg | Leu | Thr | Pro | Gln | Ala |
| 225 | | | | | 230 | | | | | 235 | | | | | 240 |
| Phe | Ser | His | Phe | Thr | Phe | Glu | Arg | Ser | Gly | His | Gln | Met | Met | Val | Val |
| | | | | 245 | | | | | 250 | | | | | 255 | |
| Asp | Ile | Gln | Gly | Val | Gly | Asp | Leu | Tyr | Thr | Asp | Pro | Gln | Ile | His | Thr |
| | | | 260 | | | | | 265 | | | | | 270 | | |
| Val | Val | Gly | Thr | Asp | Tyr | Gly | Asp | Gly | Asn | Leu | Gly | Thr | Arg | Gly | Met |
| | | | 275 | | | | | 280 | | | | | 285 | | |
| Ala | Leu | Phe | Phe | His | Ser | His | Arg | Cys | Asn | Asp | Ile | Cys | Glu | Thr | Met |
| | | 290 | | | | | 295 | | | | | 300 | | | |
| Asp | Leu | Ser | Asn | Phe | Glu | Leu | Ser | Pro | Pro | Glu | Ile | Glu | Ala | Thr | Glu |
| 305 | | | | | 310 | | | | | 315 | | | | | 320 |
| Val | Ala | Met | Glu | Val | Ala | Ala | Lys | Gln | Lys | Ser | Cys | Ile | Val | Pro | |
| | | | 325 | | | | | 330 | | | | | 335 | | |
| Pro | Thr | Val | Phe | Glu | Ala | Arg | Arg | Asn | Arg | Ile | Ser | Ser | Glu | Cys | Val |
| | | | 340 | | | | | 345 | | | | | 350 | | |
| His | Val | Glu | His | Gly | Ile | Ser | Met | Asp | Gln | Leu | Arg | Lys | Arg | Lys | Thr |
| | | | 355 | | | | | 360 | | | | | 365 | | |
| Leu | Asn | Gln | Ser | Ser | Thr | Asp | Leu | Ser | Ala | Lys | Ser | His | Asn | Glu | Asp |
| | | 370 | | | | | 375 | | | | | 380 | | | |
| Cys | Val | Cys | Pro | Glu | Cys | Ile | Pro | Val | Val | Glu | Gln | Leu | Cys | Glu | Pro |
| 385 | | | | | 390 | | | | | 395 | | | | | 400 |
| Cys | Ser | Glu | Asp | Glu | Glu | Asp | Glu | Glu | Glu | Asp | Tyr | Pro | Arg | Ser | Glu |

```
                405                 410                 415
Lys Ser Gly Asn Ser Gln Lys Ser Arg Arg Ser Arg Met Ser Ile Ser
            420                 425                 430

Thr Arg Ser Ser Gly Asp Glu Ser Ala Ser Arg Pro Arg Lys Cys Gly
            435                 440                 445

Phe Val Asp Leu Asn Ser Leu Arg Gln Arg His Asp Ser Phe Arg Ser
        450                 455                 460

Ser Val Gly Thr Tyr Ser Met Asn Ser Ser Arg Gln Thr Arg Asp Thr
465                 470                 475                 480

Glu Lys Asp Glu Phe Trp Lys Val Leu Arg Lys Gln Ser Val Pro Ala
                485                 490                 495

Asn Ile Leu Ser Leu Gln Leu Gln Gln Met Ala Ala Asn Leu Glu Asn
            500                 505                 510

Asp Glu Asp Val Pro Gln Val Thr Gly His Gln Phe Ser Val Leu Gly
        515                 520                 525

Gln Ile His Ile Asp Leu Ser Arg Tyr His Glu Leu Gly Arg Phe Val
530                 535                 540

Glu Val Asp Ser Glu His Lys Glu Met Leu Glu Gly Ser Glu Asn Asp
545                 550                 555                 560

Ala Arg Val Pro Ile Lys Tyr Asp Lys Gln Ser Ala Ile Phe His Leu
                565                 570                 575

Asp Ile Ala Arg Lys Cys Gly Ile Leu Glu Ala Val Leu Thr Ser Ala
            580                 585                 590

His Ile Val Leu Gly Leu Pro His Glu Leu Leu Lys Glu Val Thr Val
        595                 600                 605

Asp Asp Leu Phe Pro Asn Gly Phe Gly Glu Gln Glu Asn Gly Ile Arg
610                 615                 620

Ala Asp Lys Gly Gln Lys Pro Cys Asp Leu Glu Glu Phe Gly Ser Asp
625                 630                 635                 640

Leu Met Glu Ile Ala Ala Glu Met Gly Asp Lys Gly Ala Met Leu Tyr
                645                 650                 655

Met Ala His Ala Tyr Glu Thr Gly Gln His Leu Gly Pro Asn Arg Arg
            660                 665                 670

Thr Asp Tyr Lys Lys Ser Ile Asp Trp Tyr Gln Arg Val Val Gly Phe
        675                 680                 685

Gln Glu Glu Glu Glu Leu Asp Ser Asp Cys Gly Lys Thr Thr Phe Ser
690                 695                 700

Ser Phe Ala Pro Leu Thr Arg His Glu Ile Leu Ala Lys Met Ala Glu
705                 710                 715                 720

Met Tyr Lys Glu Gly Gly Tyr Gly Leu Asn Gln Asp Phe Glu Arg Ala
                725                 730                 735

Tyr Gly Leu Phe Asn Glu Ala Ala Glu Ala Ala Met Glu Ala Met Asn
            740                 745                 750

Gly Lys Leu Ala Asn Lys Tyr Tyr Glu Lys Ala Glu Met Cys Gly Glu
        755                 760                 765

(2) INFORMATION FOR SEQ ID NO:11:

(i) SEQUENCE CHARACTERISTICS:
        (A) LENGTH: 2283 base pairs
        (B) TYPE: nucleic acid
        (C) STRANDEDNESS: double
        (D) TOPOLOGY: linear (ii) MOLECULE TYPE: cDNA
```

(iii) HYPOTHETICAL: NO (vi) ORIGINAL SOURCE:
    (A) ORGANISM: C. elegans (xi) SEQUENCE DESCRIPTION: SEQ ID NO:11:

| | | | | | |
|---|---|---|---|---|---|
| ATGACGATCG | ACACAACAAA | TGAGAGCGAC | AATAGTCCAA | CTAACTCACC | AGGATTGGAG | 60 |
| GCCTCGGCTC | GGACATTCTC | GCTCAATGCG | TCAAAAATGG | TTCGGATAAC | CGACGACTAC | 120 |
| GCAGATGAAG | TGTTCATTGA | ACAGAATGAT | GTCGTTATCG | AGAAGCCTCG | TATGGATCCT | 180 |
| CTCCACGTTA | GAAAACTTAT | GGAGACATGG | CGCAAGGCTG | CTCGCCGAGC | AAGAACAAAC | 240 |
| TATATAGATC | CATGGGATGA | GTTCAACATC | CACGAGTATC | CAGTACAACG | AGCTAAACGA | 300 |
| TATAGGTATT | CTGCAATCAG | AAAGCAATGG | ACAGAGGATA | TAGTCGATGT | GAGACTTCAT | 360 |
| CCGGACAGTT | TTGCACGTGG | AGCCATGCGA | GAATGCTACC | GACTCAAAAA | GTGCTCCAAG | 420 |
| CACGGAACAA | GTCAAGATTG | GAGCAGCAAC | TATGTCGCAA | AAAGATACAT | TTGTCAAGTC | 480 |
| GATCGTAGAG | TTCTTTTCGA | TGATGTCAGA | CTTCAGATGG | ATGCCAAATT | ATGGGCTGAA | 540 |
| GAATATAATC | GGTATAATCC | ACCGAAGAAA | ATTGATATTG | TTCAAATGTG | TGTCATTGAG | 600 |
| ATGATTGATG | TAAAAGGTTC | TCCACTCTAT | CATTTGGAGC | ATTTCATCGA | GGGAAAATAT | 660 |
| ATAAAATACA | ATTCAAACTC | AGGATTTGTA | TCAAATGCAG | CTCGTCTTAC | ACCACAAGCA | 720 |
| TTTTCTCACT | TCACCTTCGA | ACGTTCTGGT | CATCAAATGA | TGGTTGTCGA | TATTCAAGGA | 780 |
| GTTGGTGATC | TTTACACAGA | TCCTCAGATT | CATACAGTTG | TGGGAACTGA | TTATGGAGAT | 840 |
| GGAAACCTCG | GAACTCGTGG | AATGGCTCTT | TTCTTCCATT | CACACAGATG | TAACGATATT | 900 |
| TGTGAGACAA | TGGATCTATC | AAATTTCGAA | CTTTCGCCAC | CTGAAATCGA | GGCTACCGAA | 960 |
| GTTGCGATGG | AAGTAGCTGC | AAAGCAGAAA | AAGTCATGCA | TAGTTCCTCC | AACTGTGTTC | 1020 |
| GAAGCAAGAA | GAAATCGAAT | TTCAAGTGAA | TGTGTACATG | TCGAGCATGG | TATTTCGATG | 1080 |
| GATCAATTGA | GAAAAAGGAA | GACGTTGAAT | CAATCGTCAA | CCGATTTGTC | AGCAAAGAGT | 1140 |
| CACAACGAAG | ACTGTGTATG | TCCTGAGTGT | ATTCCAGTTG | TTGAGCAACT | CTGTGAGCCT | 1200 |
| TGCTCCGAAG | ATGAAGAGGA | CGAAGAAGAA | GACTATCCAA | GAAGTGAAAA | AGTGGAAAT | 1260 |
| AGTCAGAAAA | GTCGACGTAG | TAGAATGAGC | ATTTCAACGA | GATCTTCTGG | CGATGAATCA | 1320 |
| GCATCTCGTC | CTAGAAAATG | CGGATTTGTA | GATTTAAACT | CACTTCGTCA | GAGACATGAT | 1380 |
| AGCTTCAGAA | GTTCTGTTGG | GACATATTCT | ATGAATAGTT | CTAGACAAAC | CAGAGACACT | 1440 |
| GAAAAGGATG | AATTCTGGAA | GGTTCTTCGA | AAACAATCAG | TTCCAGCAAA | CATTCTATCA | 1500 |
| CTTCAACTTC | AACAAATGGC | TGCTAACCTG | GAAAATGATG | AAGACGTACC | ACAAGTCACC | 1560 |
| GGGCATCAGT | TCTCTGTCCT | CGGTCAGATT | CATATTGATC | TCTCACGATA | TCATGAGCTC | 1620 |
| GGGCGGTTCG | TAGAAGTTGA | TTCAGAACAT | AAGGAAATGC | TTGAGGGAAG | TGAAAATGAC | 1680 |
| GCTCGTGTAC | CAATCAAATA | CGACAAGCAG | TCTGCAATTT | TCCATTTGGA | TATCGCTCGG | 1740 |
| AAGTGTGGAA | TCCTTGAGGC | TGTGCTAACA | TCGGCTCATA | TTGTTCTCGG | ATTACCACAT | 1800 |
| GAATTGTTGA | AAGAAGTCAC | CGTTGATGAT | CTGTTTCCTA | TGGGTTTGG | AGAACAGGAA | 1860 |
| AATGGAATTC | GAGACCTAGA | AGAGTTCGGC | TCCGATCTGA | TGGAAATTGC | TGCAGAGATG | 1920 |
| GGTGATAAGG | GTGCAATGCT | GTACATGGCA | CACGCTTATG | AAACTGGTCA | GCATCTCGGA | 1980 |
| CCGAATCGAA | GAACGGATTA | TAAGAAATCG | ATTGATTGGT | ATCAACGCGT | CGTTGGATTC | 2040 |
| CAAGAAGAAG | AAGAACTTGA | CTCTGATTGT | GGAAAAACGA | CATTCTCCTC | ATTTGCTCCA | 2100 |

-continued

```
CTGACTCGTC ACGAGATTCT AGCCAAAATG GCTGAAATGT ACAAAGAGGG AGGTTATGGC      2160

CTGAATCAAG ACTTCGAACG AGCATATGGT CTATTCAATG AAGCTGCTGA AGCAGCAATG      2220

GAAGCAATGA ATGGAAAGCT CGCAAATAAA TACTATGAAA AAGCGGAAAT GTGTGGAGAA      2280

TGA                                                                    2283
```

(2) INFORMATION FOR SEQ ID NO:12:

(i) SEQUENCE CHARACTERISTICS:
        (A) LENGTH: 760 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: C. elegans (xi) SEQUENCE DESCRIPTION: SEQ ID NO:12:

```
Met Thr Ile Asp Thr Thr Asn Glu Ser Asp Asn Ser Pro Thr Asn Ser
1               5                   10                  15

Pro Gly Leu Glu Ala Ser Ala Arg Thr Phe Ser Leu Asn Ala Ser Lys
            20                  25                  30

Met Val Arg Ile Thr Asp Asp Tyr Ala Asp Glu Val Phe Ile Glu Gln
        35                  40                  45

Asn Asp Val Val Ile Glu Lys Pro Arg Met Asp Pro Leu His Val Arg
    50                  55                  60

Lys Leu Met Glu Thr Trp Arg Lys Ala Ala Arg Arg Ala Arg Thr Asn
65                  70                  75                  80

Tyr Ile Asp Pro Trp Asp Glu Phe Asn Ile His Glu Tyr Pro Val Gln
                85                  90                  95

Arg Ala Lys Arg Tyr Arg Tyr Ser Ala Ile Arg Lys Gln Trp Thr Glu
            100                 105                 110

Asp Ile Val Asp Val Arg Leu His Pro Asp Ser Phe Ala Arg Gly Ala
        115                 120                 125

Met Arg Glu Cys Tyr Arg Leu Lys Lys Cys Ser Lys His Gly Thr Ser
    130                 135                 140

Gln Asp Trp Ser Ser Asn Tyr Val Ala Lys Arg Tyr Ile Cys Gln Val
145                 150                 155                 160

Asp Arg Arg Val Leu Phe Asp Asp Val Arg Leu Gln Met Asp Ala Lys
                165                 170                 175

Leu Trp Ala Glu Glu Tyr Asn Arg Tyr Asn Pro Pro Lys Lys Ile Asp
            180                 185                 190

Ile Val Gln Met Cys Val Ile Glu Met Ile Asp Val Lys Gly Ser Pro
        195                 200                 205

Leu Tyr His Leu Glu His Phe Ile Glu Gly Lys Tyr Ile Lys Tyr Asn
    210                 215                 220

Ser Asn Ser Gly Phe Val Ser Asn Ala Ala Arg Leu Thr Pro Gln Ala
225                 230                 235                 240

Phe Ser His Phe Thr Phe Glu Arg Ser Gly His Gln Met Met Val Val
                245                 250                 255

Asp Ile Gln Gly Val Gly Asp Leu Tyr Thr Asp Pro Gln Ile His Thr
            260                 265                 270

Val Val Gly Thr Asp Tyr Gly Asp Gly Asn Leu Gly Thr Arg Gly Met
```

-continued

```
                275                 280                 285
Ala Leu Phe Phe His Ser His Arg Cys Asn Asp Ile Cys Glu Thr Met
290                 295                 300
Asp Leu Ser Asn Phe Glu Leu Ser Pro Pro Glu Ile Glu Ala Thr Glu
305                 310                 315                 320
Val Ala Met Glu Val Ala Ala Lys Gln Lys Lys Ser Cys Ile Val Pro
                325                 330                 335
Pro Thr Val Phe Glu Ala Arg Arg Asn Arg Ile Ser Ser Glu Cys Val
                340                 345                 350
His Val Glu His Gly Ile Ser Met Asp Gln Leu Arg Lys Arg Lys Thr
                355                 360                 365
Leu Asn Gln Ser Ser Thr Asp Leu Ser Ala Lys Ser His Asn Glu Asp
370                 375                 380
Cys Val Cys Pro Glu Cys Ile Pro Val Val Glu Gln Leu Cys Glu Pro
385                 390                 395                 400
Cys Ser Glu Asp Glu Glu Asp Glu Glu Glu Asp Tyr Pro Arg Ser Glu
                405                 410                 415
Lys Ser Gly Asn Ser Gln Lys Ser Arg Arg Ser Arg Met Ser Ile Ser
                420                 425                 430
Thr Arg Ser Ser Gly Asp Glu Ser Ala Ser Arg Pro Arg Lys Cys Gly
                435                 440                 445
Phe Val Asp Leu Asn Ser Leu Arg Gln Arg His Asp Ser Phe Arg Ser
450                 455                 460
Ser Val Gly Thr Tyr Ser Met Asn Ser Ser Arg Gln Thr Arg Asp Thr
465                 470                 475                 480
Glu Lys Asp Glu Phe Trp Lys Val Leu Arg Lys Gln Ser Val Pro Ala
                485                 490                 495
Asn Ile Leu Ser Leu Gln Leu Gln Gln Met Ala Ala Asn Leu Glu Asn
                500                 505                 510
Asp Glu Asp Val Pro Gln Val Thr Gly His Gln Phe Ser Val Leu Gly
                515                 520                 525
Gln Ile His Ile Asp Leu Ser Arg Tyr His Glu Leu Gly Arg Phe Val
                530                 535                 540
Glu Val Asp Ser Glu His Lys Glu Met Leu Glu Gly Ser Glu Asn Asp
545                 550                 555                 560
Ala Arg Val Pro Ile Lys Tyr Asp Lys Gln Ser Ala Ile Phe His Leu
                565                 570                 575
Asp Ile Ala Arg Lys Cys Gly Ile Leu Glu Ala Val Leu Thr Ser Ala
                580                 585                 590
His Ile Val Leu Gly Leu Pro His Glu Leu Leu Lys Glu Val Thr Val
                595                 600                 605
Asp Asp Leu Phe Pro Asn Gly Phe Gly Glu Gln Glu Asn Gly Ile Arg
610                 615                 620
Asp Leu Glu Glu Phe Gly Ser Asp Leu Met Glu Ile Ala Ala Glu Met
625                 630                 635                 640
Gly Asp Lys Gly Ala Met Leu Tyr Met Ala His Ala Tyr Glu Thr Gly
                645                 650                 655
Gln His Leu Gly Pro Asn Arg Arg Thr Asp Tyr Lys Lys Ser Ile Asp
                660                 665                 670
Trp Tyr Gln Arg Val Val Gly Phe Gln Glu Glu Glu Leu Asp Ser
                675                 680                 685
Asp Cys Gly Lys Thr Thr Phe Ser Ser Phe Ala Pro Leu Thr Arg His
```

|     | 690 | 695 | 700 |
| --- | --- | --- | --- |

Glu Ile Leu Ala Lys Met Ala Glu Met Tyr Lys Glu Gly Gly Tyr Gly
705                     710                    715                    720

Leu Asn Gln Asp Phe Glu Arg Ala Tyr Gly Leu Phe Asn Glu Ala Ala
                725                     730                    735

Glu Ala Ala Met Glu Ala Met Asn Gly Lys Leu Ala Asn Lys Tyr Tyr
                740                    745                    750

Glu Lys Ala Glu Met Cys Gly Glu
            755                    760

(2) INFORMATION FOR SEQ ID NO:13:

(i) SEQUENCE CHARACTERISTICS:
        (A) LENGTH: 628 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Dictyostelium discoideum (xi) SEQUENCE DESCRIPTION: SEQ ID NO:13:

```
GTATTGTATG TGTTTCAATT GAGAAGACTC CATTTGCAAA GGGTAGTTGT AGAACAGCAC     60
ATAAATTAAA GGATTGGAGT CAACCAGATC AAGGATTAGT TGGTAAATTT TCAACCAATA    120
AAAAGACGAC AAGAGATTCA TACTTTACAG ATGTATTGAT GCAAACATTT TGTGCTAAAT    180
GGGCAGAGAA ATTCAATGAA GCGAAACCAC CAAAACCAAT TACATTCTTA CCATCATACG    240
TTTACGAATT GATTGATCAT CCACCACCTT ATCCAGTTTG TGGTGGTGAA CCATTCATTG    300
AGGGAGATTA CAAGAAACAT AACAACAACA GTGGTTACGT TAGTAGTGAT GCTAGAAATA    360
CACCACAATC ATTCTCTCAT TTCTCATACG AACTCTCCAA TCATGAATTG TTGATCGTTG    420
ATATCCAAGG TGTCAACGAT TTCTACACTG ATCCTCAAAT TCATACGAAA TCAGGCGAGG    480
GCTTTGGCGA GGGTAATTTG GGCGAGACGG GTTTCCACAA ATTCCTTCAA ACACACAAGT    540
GTAATCCAGT TTGTGACTTT TTAAAGTTGA AACCAATCAA TCAATCAAAG AAAGCCCTCC    600
TAAGAGGTAC ATTACCCGTC GTACAATT                                      628
```

(2) INFORMATION FOR SEQ ID NO:14:

(i) SEQUENCE CHARACTERISTICS:
        (A) LENGTH: 209 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Dictyostelium discoideum (xi) SEQUENCE DESCRIPTION: SEQ ID NO:14:

Ile Val Cys Val Ser Ile Glu Lys Thr Pro Phe Ala Lys Gly Ser Cys
1                       5                      10                     15

Arg Thr Ala His Lys Leu Lys Asp Trp Ser Gln Pro Asp Gln Gly Leu
                20                     25                     30

-continued

```
Val Gly Lys Phe Ser Thr Asn Lys Thr Thr Arg Asp Ser Tyr Phe
        35                  40                  45

Thr Asp Val Leu Met Gln Thr Phe Cys Ala Lys Trp Ala Glu Lys Phe
 50                  55                  60

Asn Glu Ala Lys Pro Pro Lys Pro Ile Thr Phe Leu Pro Ser Tyr Val
 65                  70                  75                  80

Tyr Glu Leu Ile Asp His Pro Pro Tyr Pro Val Cys Gly Gly Glu
                 85                  90                  95

Pro Phe Ile Glu Gly Asp Tyr Lys Lys His Asn Asn Asn Ser Gly Tyr
                100                 105                 110

Val Ser Ser Asp Ala Arg Asn Thr Pro Gln Ser Phe Ser His Phe Ser
                115                 120                 125

Tyr Glu Leu Ser Asn His Glu Leu Leu Ile Val Asp Ile Gln Gly Val
130                 135                 140

Asn Asp Phe Tyr Thr Asp Pro Gln Ile His Thr Lys Ser Gly Glu Gly
145                 150                 155                 160

Phe Gly Glu Gly Asn Leu Gly Glu Thr Gly Phe His Lys Phe Leu Gln
                165                 170                 175

Thr His Lys Cys Asn Pro Val Cys Asp Phe Leu Lys Leu Lys Pro Ile
                180                 185                 190

Asn Gln Ser Lys Lys Ala Leu Leu Arg Gly Thr Leu Pro Val Val Gln
                195                 200                 205

Leu
```

(2) INFORMATION FOR SEQ ID NO:15:

(i) SEQUENCE CHARACTERISTICS:
    (A) LENGTH: 238 amino acids
    (B) TYPE: amino acid
    (C) STRANDEDNESS: single
    (D) TOPOLOGY: linear (ii) MOLECULE TYPE: protein (iii) HYPOTHETICAL: NO (vi) ORIGINAL SOURCE:
    (A) ORGANISM: Homo sapiens (xi) SEQUENCE DESCRIPTION: SEQ ID NO:15:

```
Gly Glu Trp Leu Asp Asp Glu Val Leu Ile Lys Met Ala Ser Gln Pro
 1               5                  10                  15

Phe Gly Arg Gly Ala Met Arg Glu Cys Phe Arg Thr Lys Lys Leu Ser
                20                  25                  30

Asn Phe Leu His Ala Gln Gln Trp Lys Gly Ala Ser Asn Tyr Val Ala
                35                  40                  45

Lys Arg Tyr Ile Glu Pro Val Asp Arg Asp Val Tyr Phe Glu Asp Val
 50                  55                  60

Arg Leu Gln Met Glu Ala Lys Leu Trp Gly Glu Tyr Asn Arg His
 65                  70                  75                  80

Lys Pro Pro Lys Gln Val Asp Ile Met Gln Met Cys Ile Ile Glu Leu
                85                  90                  95

Lys Asp Arg Pro Gly Lys Pro Leu Phe His Leu Glu His Tyr Ile Glu
                100                 105                 110

Gly Lys Tyr Ile Lys Tyr Asn Ser Asn Ser Gly Phe Val Arg Asp Asp
                115                 120                 125

Asn Ile Arg Leu Thr Pro Gln Ala Phe Ser His Phe Thr Phe Glu Arg
```

-continued

```
              130                 135                 140
Ser Gly His Gln Leu Ile Val Val Asp Ile Gln Gly Val Gly Asp Leu
145                 150                 155                 160

Tyr Thr Asp Pro Gln Ile His Thr Glu Thr Gly Thr Asp Phe Gly Asp
                165                 170                 175

Gly Asn Leu Gly Val Arg Gly Met Ala Leu Phe Phe Tyr Ser His Ala
                180                 185                 190

Cys Asn Arg Ile Cys Glu Ser Met Gly Leu Ala Pro Phe Asp Leu Ser
                195                 200                 205

Pro Arg Glu Arg Asp Ala Val Asn Gln Asn Thr Lys Leu Leu Gln Ser
    210                 215                 220

Ala Lys Thr Ile Leu Arg Gly Thr Glu Lys Cys Gly Ser
225                 230                 235
```

(2) INFORMATION FOR SEQ ID NO:16:

(i) SEQUENCE CHARACTERISTICS:
        (A) LENGTH: 258 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: D. discoideum (xi) SEQUENCE DESCRIPTION: SEQ ID NO:16:

```
Asn Lys Trp Ile Arg Leu Ser Met Lys Leu Lys Val Glu Arg Lys Pro
1               5                   10                  15

Phe Ala Glu Gly Ala Leu Arg Glu Ala Tyr His Thr Val Ser Leu Gly
                20                  25                  30

Val Gly Thr Asp Glu Asn Tyr Pro Leu Gly Thr Thr Thr Lys Leu Phe
            35                  40                  45

Pro Pro Ile Glu Met Ile Ser Pro Ile Ser Lys Asn Asn Glu Ala Met
        50                  55                  60

Thr Gln Leu Lys Asn Gly Thr Lys Phe Val Leu Lys Leu Tyr Lys Lys
65                  70                  75                  80

Glu Ala Glu Gln Gln Ala Ser Arg Glu Leu Tyr Phe Glu Asp Val Lys
                85                  90                  95

Met Gln Met Val Cys Arg Asp Trp Gly Asn Lys Phe Asn Gln Lys Lys
                100                 105                 110

Pro Pro Lys Lys Ile Glu Phe Leu Met Ser Trp Val Val Glu Leu Ile
        115                 120                 125

Asp Arg Ser Pro Ser Ser Asn Gly Gln Pro Ile Leu Cys Ser Ile Glu
    130                 135                 140

Pro Leu Leu Val Gly Glu Phe Lys Lys Asn Asn Ser Asn Tyr Gly Ala
145                 150                 155                 160

Val Leu Thr Asn Arg Ser Thr Pro Gln Ala Phe Ser His Phe Thr Tyr
                165                 170                 175

Glu Leu Ser Asn Lys Gln Met Ile Val Val Asp Ile Gln Gly Val Asp
                180                 185                 190

Asp Leu Tyr Thr Asp Pro Gln Ile His Thr Pro Asp Gly Lys Gly Phe
                195                 200                 205

Gly Leu Gly Asn Leu Gly Lys Ala Gly Ile Asn Lys Phe Ile Thr Thr
```

```
                    210                 215                 220
His Lys Cys Asn Ala Val Cys Ala Leu Leu Asp Leu Asp Val Lys Leu
225                 230                 235                 240

Gly Gly Val Leu Ser Gly Asn Asn Lys Lys Gln Leu Gln Gln Gly Thr
                    245                 250                 255

Met Val
```

(2) INFORMATION FOR SEQ ID NO:17:

(i) SEQUENCE CHARACTERISTICS:
        (A) LENGTH: 212 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: D. discoideum (xi) SEQUENCE DESCRIPTION: SEQ ID NO:17:

```
Ala Gln Trp Thr Cys Thr Ala Thr Leu Val Lys Val Glu Pro Val Pro
1                   5                  10                  15

Phe Ala Glu Gly Ala Phe Arg Lys Ala Tyr His Thr Leu Asp Leu Ser
                    20                  25                  30

Lys Ser Gly Ala Ser Gly Arg Tyr Val Ser Lys Ile Gly Lys Lys Pro
                    35                  40                  45

Thr Pro Arg Pro Ser Tyr Phe Glu Asp Val Lys Met Gln Met Ile Ala
                    50                  55                  60

Lys Lys Trp Ala Asp Lys Tyr Asn Ser Phe Lys Pro Pro Lys Lys Ile
65                  70                  75                  80

Glu Phe Leu Gln Ser Cys Val Leu Glu Phe Val Asp Arg Thr Ser Ser
                    85                  90                  95

Asp Leu Ile Cys Gly Ala Glu Pro Tyr Val Glu Gly Gln Tyr Arg Lys
                    100                 105                 110

Tyr Asn Asn Asn Ser Gly Phe Val Ser Asn Asp Glu Arg Asn Thr Pro
                    115                 120                 125

Gln Ser Phe Ser His Phe Thr Tyr Glu His Ser Asn His Gln Leu Leu
                    130                 135                 140

Ile Ile Asp Ile Gln Gly Val Gly Asp His Tyr Thr Asp Pro Gln Ile
145                 150                 155                 160

His Thr Tyr Asp Gly Val Gly Phe Gly Ile Gly Asn Leu Gly Gln Lys
                    165                 170                 175

Gly Phe Glu Lys Phe Leu Asp Thr His Lys Cys Asn Ala Ile Cys Gln
                    180                 185                 190

Tyr Leu Asn Leu Gln Ser Ile Asn Pro Lys Ser Glu Lys Ser Asp Cys
                    195                 200                 205

Gly Thr Val Pro
    210
```

(2) INFORMATION FOR SEQ ID NO:18:

(i) SEQUENCE CHARACTERISTICS:
        (A) LENGTH: 233 amino acids
        (B) TYPE: amino acid
        (C) STRANDEDNESS: single
        (D) TOPOLOGY: linear

```
      (ii) MOLECULE TYPE: protein (iii) HYPOTHETICAL: NO (vi) ORIGINAL SOURCE:
           (A) ORGANISM: C. elegans (xi) SEQUENCE DESCRIPTION: SEQ ID NO:18:

Lys Gln Trp Thr Glu Asp Ile Val Asp Val Arg Leu His Pro Asp Ser
1               5                  10                  15

Phe Ala Arg Gly Ala Met Arg Glu Cys Tyr Arg Leu Lys Lys Cys Ser
               20                  25                  30

Lys His Gly Thr Ser Gln Asp Trp Ser Ser Asn Tyr Val Ala Lys Arg
           35                  40                  45

Tyr Ile Cys Gln Val Asp Arg Arg Val Leu Phe Asp Asp Val Arg Leu
       50                  55                  60

Gln Met Asp Ala Lys Leu Trp Ala Glu Glu Tyr Asn Arg Tyr Asn Pro
65                  70                  75                  80

Pro Lys Lys Ile Asp Ile Val Gln Met Cys Val Ile Glu Met Ile Asp
               85                  90                  95

Val Lys Gly Ser Pro Leu Tyr His Leu Glu His Phe Ile Glu Gly Lys
           100                 105                 110

Tyr Ile Lys Tyr Asn Ser Asn Ser Gly Phe Val Ser Asn Ala Ala Arg
       115                 120                 125

Leu Thr Pro Gln Ala Phe Ser His Phe Thr Phe Glu Arg Ser Gly His
130                 135                 140

Gln Met Met Val Val Asp Ile Gln Gly Val Gly Asp Leu Tyr Thr Asp
145                 150                 155                 160

Pro Gln Ile His Thr Val Val Gly Thr Asp Tyr Gly Asp Gly Asn Leu
               165                 170                 175

Gly Thr Arg Gly Met Ala Leu Phe Phe His Ser His Arg Cys Asn Asp
           180                 185                 190

Ile Cys Glu Thr Met Asp Leu Ser Asn Phe Glu Leu Ser Pro Pro Glu
       195                 200                 205

Ile Glu Ala Thr Glu Val Ala Met Glu Val Ala Ala Lys Gln Lys Lys
210                 215                 220

Ser Cys Ile Val Pro Pro Thr Val Phe
225                 230

(2) INFORMATION FOR SEQ ID NO:19:

(i) SEQUENCE CHARACTERISTICS:
          (A) LENGTH: 25 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Oligonucleotide Primer D"

(iii) HYPOTHETICAL: NO (xi) SEQUENCE DESCRIPTION: SEQ ID NO:19:

GGATTTGGAC TGGACAAGAA CCCCC                                    25

(2) INFORMATION FOR SEQ ID NO:20:

(i) SEQUENCE CHARACTERISTICS:
          (A) LENGTH: 16 amino acids
```

(B) TYPE: amino acid
            (C) STRANDEDNESS: single
            (D) TOPOLOGY: linear (ii) MOLECULE TYPE: peptide (iii) HYPOTHETICAL: NO (xi) SEQUENCE DESCRIPTION: SEQ ID NO:20:

Arg Lys Lys Phe Gly Glu Ser Glu Lys Thr Lys Thr Lys Glu Phe Leu
1               5                  10                  15

(2) INFORMATION FOR SEQ ID NO:21:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (iii) HYPOTHETICAL: NO (xi) SEQUENCE DESCRIPTION: SEQ ID NO:21:

Leu Thr Pro Gln Ala Phe Ser His Phe Thr Phe Glu Arg
1               5                  10

(2) INFORMATION FOR SEQ ID NO:22:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (xi) SEQUENCE DESCRIPTION: SEQ ID NO:22:

Leu Ala Asn Xaa Tyr Tyr Glu Lys Ala Glu
1               5                  10

(2) INFORMATION FOR SEQ ID NO:23:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides"

(iii) HYPOTHETICAL: NO (xi) SEQUENCE DESCRIPTION: SEQ ID NO:23:

CANGCNTTNN NNCANTTNAC NTTNGANNG                                              29

(2) INFORMATION FOR SEQ ID NO:24:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Oligonucleotides"

-continued

```
    (iii) HYPOTHETICAL: NO (xi) SEQUENCE DESCRIPTION: SEQ ID NO:24:

TCNGCNTTNT CNTANTANTT NTTNGC                                    26

(2) INFORMATION FOR SEQ ID NO:25:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (xi) SEQUENCE DESCRIPTION: SEQ ID NO:25:

TACAATCAGC TGATGACCAG AACGCTC                                   27
```